(12) United States Patent
Semler et al.

(10) Patent No.: US 11,278,424 B2
(45) Date of Patent: Mar. 22, 2022

(54) EXPANDABLE VERTEBRAL BODY REPLACEMENT DEVICE AND METHOD

(71) Applicant: MUSC FOUNDATION FOR RESEARCH DEVELOPMENT, Charleston, SC (US)

(72) Inventors: Mark Evald Semler, Mount Pleasant, SC (US); Bruce Frankel, Mount Pleasant, SC (US); Joseph Ruscito, Charleston, SC (US); Christopher Hapstack, Charleston, SC (US)

(73) Assignee: MUSC FOUNDATON FOR RESEARCH DEVELOPMENT, Charleston, SC (US)

( * ) Notice: Subject to any disclaimer, the term of this patent is extended or adjusted under 35 U.S.C. 154(b) by 190 days.

(21) Appl. No.: 16/424,455

(22) Filed: May 28, 2019

(65) Prior Publication Data

US 2019/0314170 A1 Oct. 17, 2019

Related U.S. Application Data

(63) Continuation-in-part of application No. PCT/US2017/031093, filed on May 4, 2017.
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/4465* (2013.01); *A61F 2/4611* (2013.01); *A61F 2002/3055* (2013.01);
(Continued)

(58) Field of Classification Search
CPC ...... A61F 2/4455; A61F 2/446; A61F 2/4465; A61F 2/447; A61F 2002/448;
(Continued)

(56) References Cited

U.S. PATENT DOCUMENTS 4,401,112 A 8/1983 Rezaian
4,553,273 A 11/1985 Wu
(Continued)

FOREIGN PATENT DOCUMENTS

WO 2010124008 10/2010
WO 2013003736 1/2013
(Continued)

OTHER PUBLICATIONS

International Search Report and Written Opinion for International Application No. PCT/US2016/020209 dated Jul. 25, 2016, 17 pages.
(Continued)

*Primary Examiner* — Jan Christopher L Merene
(74) *Attorney, Agent, or Firm* — Heslin Rothenberg Farley & Mesiti P.C.; Jacquelyn A. Graff, Esq.

(57) ABSTRACT

Expandable vertebral body implants, systems, instruments, and methods of assembly and using the implants, systems, and instruments are disclosed. The vertebral body implant includes a body with a first end and a second end, a first rotating member rotatably coupled to the first end, wherein an end includes a plurality of first notches inset into the first rotating member, a second rotating member rotatably coupled to the second end, wherein an end includes a plurality of second notches inset into the second rotating member, a first extension member moveably coupled to the first end, and a second extension member moveably coupled to the second end. The expandable cage system comprises a vertebral body implant and an insertion instrument. Methods
(Continued)

for assembling and using the vertebral body implants and instruments are also disclosed.

20 Claims, 33 Drawing Sheets

Related U.S. Application Data

(60) Provisional application No. 62/427,149, filed on Nov. 28, 2016.

(52) U.S. Cl.
CPC ............... *A61F 2002/30224* (2013.01); *A61F 2002/30405* (2013.01); *A61F 2002/30579* (2013.01); *A61F 2002/4627* (2013.01)

(58) Field of Classification Search
CPC ........ A61F 2002/4485; A61F 2002/449; A61F 2002/30556; A61F 2002/30601; A61F 2002/4627; A61F 2002/3055; A61F 2002/30523; A61F 2002/30525; A61F 2002/30528; A61F 2002/30545
See application file for complete search history.

(56) References Cited

U.S. PATENT DOCUMENTS

| | | | |
|---|---|---|---|
| 4,657,550 | A | 4/1987 | Daher |
| 5,083,621 | A | 1/1992 | Sheridan |
| 5,336,223 | A | 8/1994 | Rogers |
| 5,571,192 | A | 11/1996 | Schonhoffer |
| 5,702,453 | A | 12/1997 | Rabbe |
| 5,702,455 | A | 12/1997 | Saggar |
| 5,776,198 | A * | 7/1998 | Rabbe .................... A61B 17/70 623/17.15 |
| 5,989,290 | A | 11/1999 | Biedermann |
| 6,176,881 | B1 | 1/2001 | Schar |
| 6,344,057 | B1 * | 2/2002 | Rabbe ................. A61F 2/30744 623/17.11 |
| 6,524,341 | B2 | 2/2003 | Lang |
| 6,730,088 | B2 | 5/2004 | Yeh |
| 6,752,832 | B2 | 6/2004 | Neumann |
| 6,802,867 | B2 | 10/2004 | Manasas |
| 6,902,579 | B2 | 6/2005 | Harms |
| 7,056,343 | B2 | 6/2006 | Schafer |
| 7,384,431 | B2 | 6/2008 | Berry |
| 7,547,325 | B2 | 6/2009 | Biedermann |
| 7,575,601 | B2 | 8/2009 | Dickson |
| 7,588,573 | B2 | 9/2009 | Berry |
| 7,608,078 | B2 | 10/2009 | Berry |
| 7,641,693 | B2 | 1/2010 | Gutlin |
| 7,674,296 | B2 | 3/2010 | Rhoda |
| 7,758,648 | B2 | 7/2010 | Castleman |
| 7,811,327 | B2 | 10/2010 | Hansell |
| 7,879,096 | B2 | 2/2011 | Dickson |
| 7,909,870 | B2 | 3/2011 | Kraus |
| 7,914,581 | B2 | 3/2011 | Dickson |
| 7,981,157 | B2 | 7/2011 | Castleman |
| 8,142,441 | B2 | 3/2012 | Refai |
| 8,157,864 | B2 | 4/2012 | Rogeau |
| 8,182,535 | B2 | 5/2012 | Kraus |
| 8,182,537 | B2 | 5/2012 | Refai |
| 8,197,546 | B2 | 6/2012 | Doubler |
| 8,231,681 | B2 | 7/2012 | Castleman |
| 8,241,363 | B2 | 8/2012 | Sommerich |
| 8,246,680 | B2 | 8/2012 | Betz |
| 8,252,054 | B2 | 8/2012 | Greenhalgh |
| 8,267,998 | B2 | 9/2012 | Kraus |
| 8,268,004 | B2 | 9/2012 | Castleman |
| 8,282,683 | B2 | 10/2012 | McLaughlin |
| 8,292,963 | B2 | 10/2012 | Miller |
| 8,308,802 | B2 | 11/2012 | Rhoda |
| 8,337,559 | B2 | 12/2012 | Hansell |
| 8,366,779 | B2 | 2/2013 | Dickson |
| 8,377,140 | B2 | 2/2013 | DeFalco |
| 8,540,770 | B2 | 9/2013 | Woodburn, Sr. |
| 8,568,482 | B2 | 10/2013 | Kraus |
| 8,585,763 | B2 | 11/2013 | Olevsky |
| 8,591,585 | B2 | 11/2013 | McLaughlin |
| 8,591,587 | B2 | 11/2013 | Refai |
| 8,603,173 | B2 | 12/2013 | Biedermann |
| 8,668,740 | B2 | 3/2014 | Rhoda |
| 8,690,886 | B2 | 4/2014 | Fedorov |
| 8,690,950 | B2 | 4/2014 | Refai et al. |
| 8,702,719 | B2 | 4/2014 | Refai |
| 8,721,723 | B2 | 5/2014 | Hansell |
| 8,740,980 | B2 | 6/2014 | Merves |
| 8,801,788 | B2 | 8/2014 | Merves |
| 8,870,880 | B2 | 10/2014 | Himmelberger |
| 8,992,617 | B2 | 3/2015 | Woodburn |
| 9,023,108 | B2 | 5/2015 | Hansell et al. |
| 9,034,046 | B2 | 5/2015 | Refai et al. |
| 9,050,195 | B2 | 6/2015 | DeFalco et al. |
| 9,138,324 | B2 | 9/2015 | Prevost et al. |
| 9,144,503 | B2 | 9/2015 | Stinchfield et al. |
| 9,173,747 | B2 | 11/2015 | Hansell et al. |
| 9,180,018 | B2 | 11/2015 | Hansell et al. |
| 9,192,481 | B2 | 11/2015 | Rhoda et al. |
| 9,211,193 | B2 | 12/2015 | Laubert |
| 9,241,808 | B2 | 1/2016 | Sabatino |
| 9,271,842 | B2 | 3/2016 | Davenport |
| 9,301,850 | B2 | 4/2016 | McLaughlin et al. |
| 9,320,612 | B2 | 4/2016 | Soumac |
| 9,345,588 | B2 | 5/2016 | Himmelberger et al. |
| 9,387,090 | B2 | 7/2016 | Arnold |
| 9,393,128 | B2 | 7/2016 | Hansell et al. |
| 9,474,621 | B2 | 10/2016 | McLaughlin et al. |
| 9,572,678 | B2 | 2/2017 | Nichols et al. |
| 9,579,211 | B2 | 2/2017 | McLaughlin |
| 9,636,231 | B2 | 5/2017 | Rhoda et al. |
| 9,636,233 | B2 | 5/2017 | Arnold et al. |
| 9,655,738 | B2 | 5/2017 | Stinchfield et al. |
| 9,681,961 | B2 | 6/2017 | Prevost et al. |
| 9,687,357 | B2 | 6/2017 | Bannigan et al. |
| 9,707,091 | B2 | 7/2017 | McLaughlin et al. |
| 9,707,096 | B2 | 7/2017 | Sutterlin, III et al. |
| 2004/0059271 | A1 | 3/2004 | Berry |
| 2004/0172129 | A1 * | 9/2004 | Schafer ..................... A61F 2/44 623/17.11 |
| 2004/0186569 | A1 | 9/2004 | Berry |
| 2006/0074490 | A1 | 4/2006 | Sweeney |
| 2007/0028710 | A1 * | 2/2007 | Kraus .................... A61F 2/4611 74/400 |
| 2007/0255407 | A1 | 11/2007 | Castleman |
| 2007/0255421 | A1 * | 11/2007 | Dickson .................... A61F 2/44 623/23.47 |
| 2008/0167720 | A1 | 7/2008 | Melkent |
| 2009/0112325 | A1 | 4/2009 | Refai |
| 2010/0016971 | A1 | 1/2010 | Berry |
| 2010/0094424 | A1 | 4/2010 | Woodburn |
| 2010/0211119 | A1 | 8/2010 | Refai |
| 2010/0274357 | A1 | 10/2010 | Miller |
| 2011/0087328 | A1 | 4/2011 | Dickson |
| 2011/0184524 | A1 | 7/2011 | Wiedenbeck |
| 2012/0197403 | A1 | 8/2012 | Merves |
| 2012/0265303 | A1 * | 10/2012 | Refai ........................ A61F 2/44 623/17.11 |
| 2012/0330426 | A1 | 12/2012 | McLaughlin |
| 2013/0053965 | A1 | 2/2013 | Metz-Stavenhagen |
| 2013/0310938 | A1 | 11/2013 | Soumac |
| 2013/0331943 | A1 | 12/2013 | Arnold |
| 2014/0052249 | A1 | 2/2014 | Metz-Stavenhagen |
| 2014/0058517 | A1 | 2/2014 | Sabatino |
| 2014/0088708 | A1 | 3/2014 | McLaughlin |
| 2014/0107786 | A1 | 4/2014 | Geisler |
| 2014/0156006 | A1 | 6/2014 | Bannigan |
| 2014/0222151 | A1 | 8/2014 | Refai |
| 2016/0022435 | A1 | 1/2016 | Hansell et al. |
| 2016/0022436 | A1 | 1/2016 | Hansell et al. |
| 2016/0051370 | A9 | 2/2016 | Hansell et al. |
| 2016/0199192 | A1 | 7/2016 | McLaughlin et al. |
| 2016/0235553 | A1 | 8/2016 | Himmelberger et al. |

(56) References Cited

U.S. PATENT DOCUMENTS

| | | |
|---|---|---|
| 2016/0153742 A1 | 9/2016 | Copeland et al. |
| 2016/0278933 A1* | 9/2016 | Semler ................. A61F 2/4455 |
| 2017/0007423 A1 | 1/2017 | McLaughlin et al. |
| 2017/0143510 A1 | 5/2017 | Nichols et al. |
| 2017/0216050 A1 | 8/2017 | Semler |
| 2017/0224507 A1 | 8/2017 | Arnold et al. |

FOREIGN PATENT DOCUMENTS

| | | |
|---|---|---|
| WO | 2013003738 | 1/2013 |
| WO | 2013173682 | 11/2013 |
| WO | 2016153742 | 9/2016 |

OTHER PUBLICATIONS

Invitation to Pay Additional Fees from the International Searching Authority for International Application No. PCT/US2016/020209 dated May 17, 2016, 8 pages.
International Search Report and Written Opinion for International Application No. PCT/US2017/031093 dated Aug. 10, 2017, 11 pages.

* cited by examiner

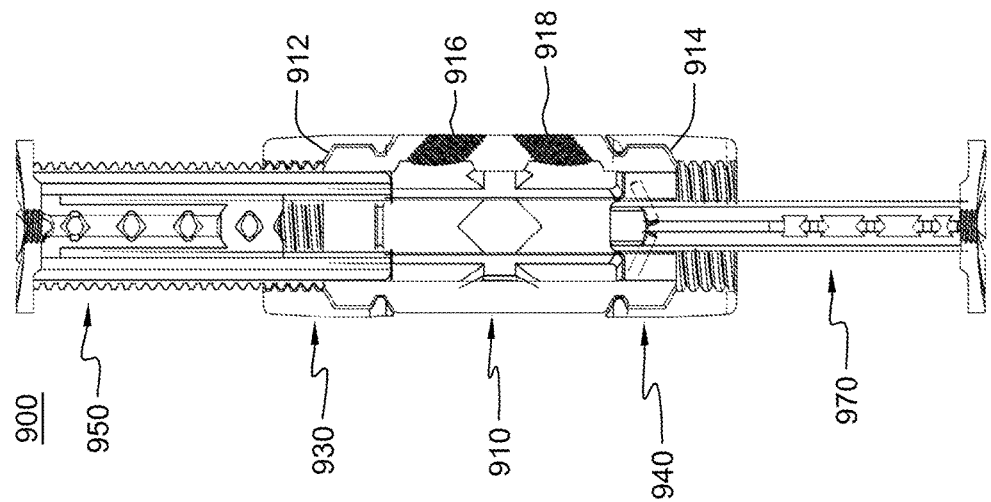
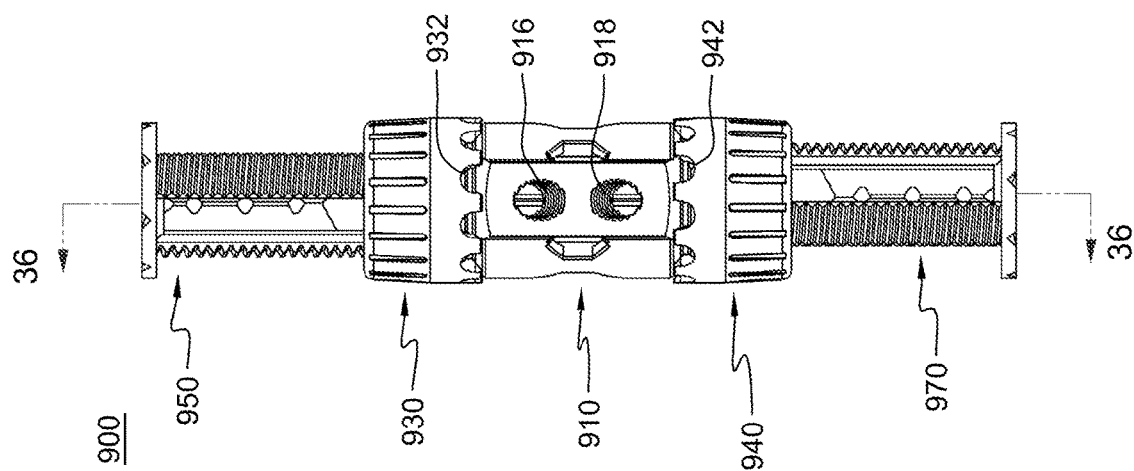

EXPANDABLE VERTEBRAL BODY REPLACEMENT DEVICE AND METHOD

CROSS REFERENCE TO RELATED APPLICATION

This application is a continuation-in-part application from PCT/US2017/031093 filed May 4, 2017 and published as WO 2018/097857 on May 31, 2018 which claims priority benefit under 35 U.S.C. § 119(e) of U.S. provisional patent application No. 62/427,149 filed Nov. 28, 2016, which are incorporated herein by reference in their entireties.

FIELD OF THE INVENTION

The present invention relates generally to a medical implants for insertion in a space between a patient's vertebrae. More specifically, but not exclusively, the present invention concerns expandable vertebral body replacement devices for implantation in a patient's spine between the vertebrae.

BACKGROUND OF THE INVENTION

Trauma or disease, such as, tumors may cause pressure on a patient's spinal cord. In order to alleviate the pressure and likely the pain it is causing, surgeons may remove part or all of a patient's vertebral bodies and adjacent vertebral discs in the location of the pressure, during a procedure, such as, a corpectomy. Often implants are used to replace the removed vertebral bodies to maintain the space between the remaining vertebral bodies.

SUMMARY OF THE INVENTION

Aspects of the present invention provide expanding vertebral body replacement devices for implantation in a patient's spine between the vertebrae and methods of using the same.

In one aspect, provided herein is a vertebral body implant, including a body with a first end and a second end, a first rotating member rotatably coupled to the first end, wherein an end includes a plurality of first notches inset into the first rotating member, a second rotating member rotatably coupled to the second end, wherein an end includes a plurality of second notches inset into the second rotating member, a first extension member moveably coupled to the first end, and a second extension member moveably coupled to the second end.

In another aspect, provided herein is an expandable cage system including a vertebral body device and an insertion instrument. The vertebral body device including a body with a first end and a second end, a first rotating member coupled to the first end, a second rotating member coupled to the second end, a first extension member moveably coupled to the first end, and a second extension member moveably coupled to the second end. The body including at least one aperture positioned on the body along a midpoint between the first end and the second end. The body also including at least one first locking hole positioned superior to the at least one aperture and at least one second locking hole positioned inferior to the at least one aperture. The insertion instrument, wherein the at least one aperture, the at least one first locking hole, and the at least one second locking hole are sized to receive the insertion instrument.

In yet another aspect, provided herein is a method for using an expandable cage system, including obtaining a vertebral body implant and an insertion instrument. The vertebral body device including a body with a first end and a second end, a first rotating member rotatably coupled to the first end, a second rotating member rotatably coupled to the second end, a first extension member moveably coupled to the first end, and a second extension member moveably coupled to the second end. The method also includes coupling the vertebral body implant to the insertion instrument and inserting the vertebral body implant into a patient between two vertebral bodies. The method further includes expanding the vertebral body implant and removing the insertion instrument.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 35 is a side view of another embodiment of a vertebral body implant, in accordance with an aspect of the present invention;

FIG. 36 is a cross-sectional view of the vertebral body implant of FIG. 35 taken along line 36-36 of FIG. 35 and showing the angled set screw openings, in accordance with an aspect of the present invention;

DETAILED DESCRIPTION FOR CARRYING OUT THE INVENTION

Figure 1:
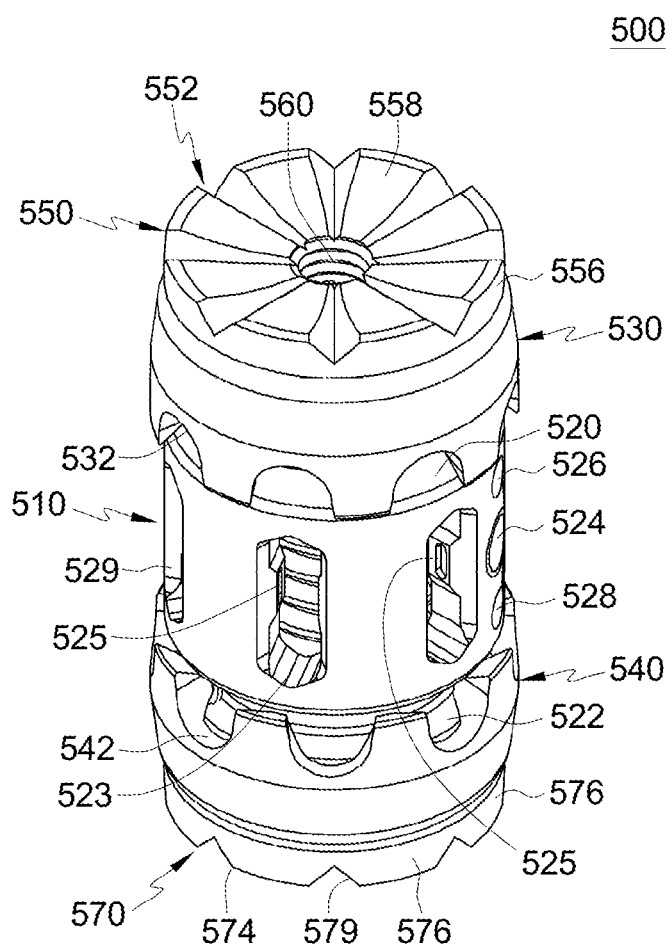
FIG. 1 is a top perspective view of an embodiment of a vertebral body implant, in accordance with an aspect of the present invention.
Figure 2:
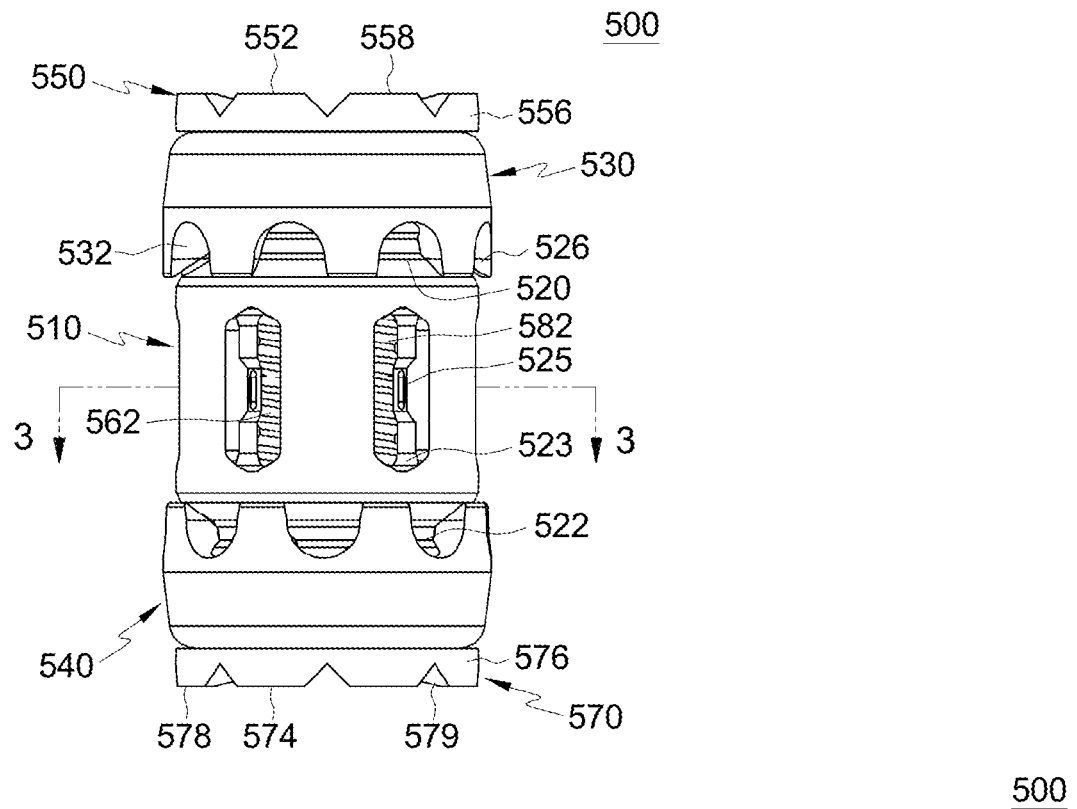
FIG. 2 is a side view of the implant of FIG. 1, in accordance with an aspect of the present invention.
Figure 3:
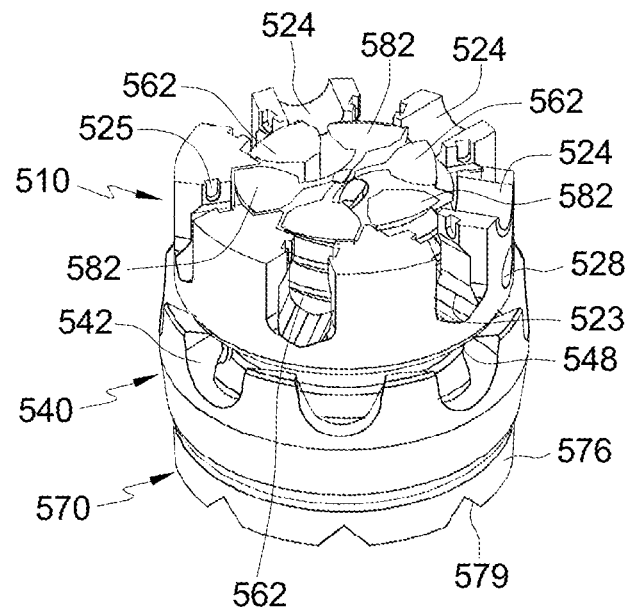
FIG. 3 is a cross-sectional view of the implant of FIG. 1 taken along line 3-3 in FIG. 58, in accordance with an aspect of the present invention.

Generally stated, disclosed herein is an expandable vertebral body replacement device. Further, methods of assembling and using the expandable vertebral body replacement device are discussed.

In this detailed description and the following claims, the words proximal, distal, anterior, posterior, medial, lateral, superior, inferior, cephalad, and caudal are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above, "inferior" means a direction below another object or structure, "cephalad" means a direction toward the head, and "caudal" means a direction toward the inferior part of the body.

Referring to the drawings, wherein like reference numerals are used to indicate like or analogous components throughout the several views, and with particular reference to FIGS. 1-5, there is illustrated an exemplary embodiment of a vertebral body replacement implant 500. The vertebral body implant 500 may include a body 510, a first rotating member 530 rotatably coupled to the first end 512 of the body 510, a second rotating member 540 rotatably coupled to the second end 514 of the body 510, a first extension member 550 moveably coupled to a first end 512 of the body 510, and a second extension member 570 moveably coupled to a second end 514 of the body 510.

As shown in FIGS. 4-11, the body 510 may include an opening 516 extending from the first end 512 to the second end 514, for example, along the longitudinal axis of the body 510. The opening 516 may include at least two channels 517, 518, 519 extending into the body 510 from the opening 516. At least one first channel 517 may extend from the first end 512 toward the second end 514 and at least one second channel 518 may extend from the second end 514 toward the first end 512. At least one third channel 519 may extend from the first end 512 to the second end 514. In the depicted embodiment, the at least one first channel 517 may be one first channel 517, the at least one second channel 518 may be one second channel 518, and the at least one third channel 519 may be, for example, four channels 519. The channels 517, 518, 519 may be, for example, evenly spaced around the opening 516. As shown, the body 510 may include, for example, one first channel 517 open on the first end 512, one second channel 518 open on the second end 514, and four third channels 519 open on both the first and second ends 512, 514. Alternative numbers of channels 517, 518, 519 are also contemplated, for example, the body 510 may include more or less channels 517, 518, 519.

Figure 4:
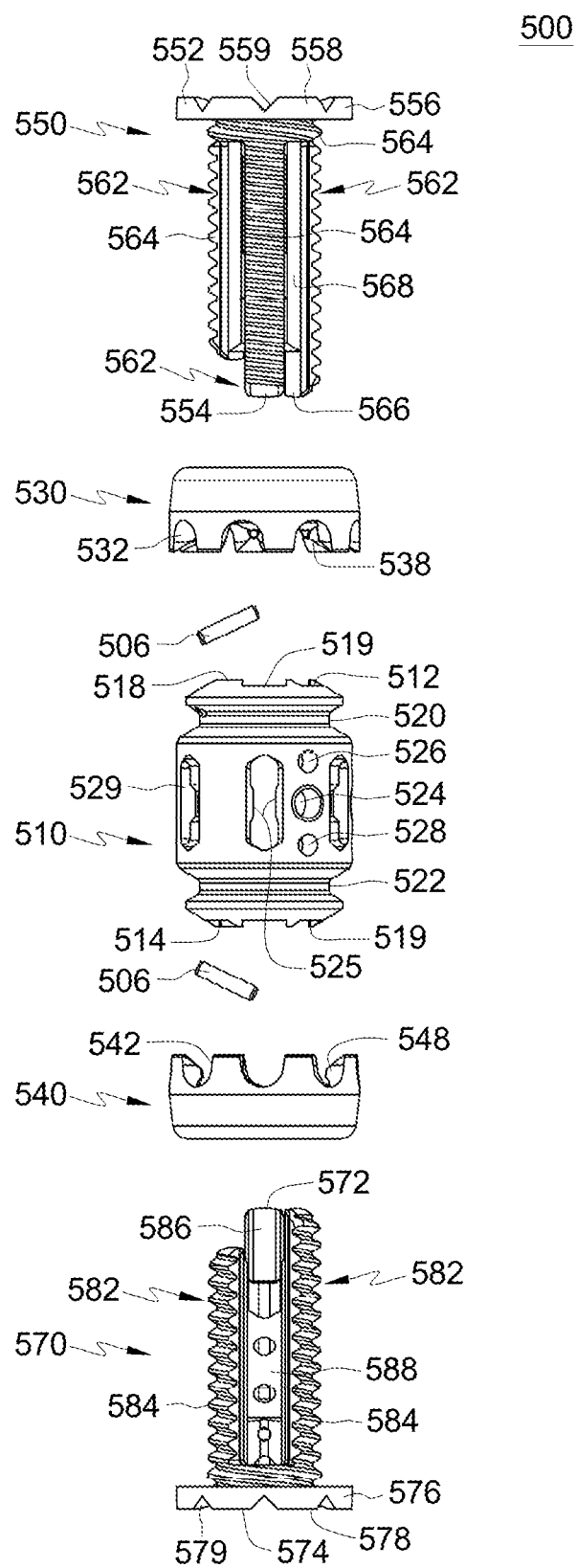
FIG. 4 is an exploded side view of the implant of FIG. 1, in accordance with an aspect of the present invention.
Figure 5:
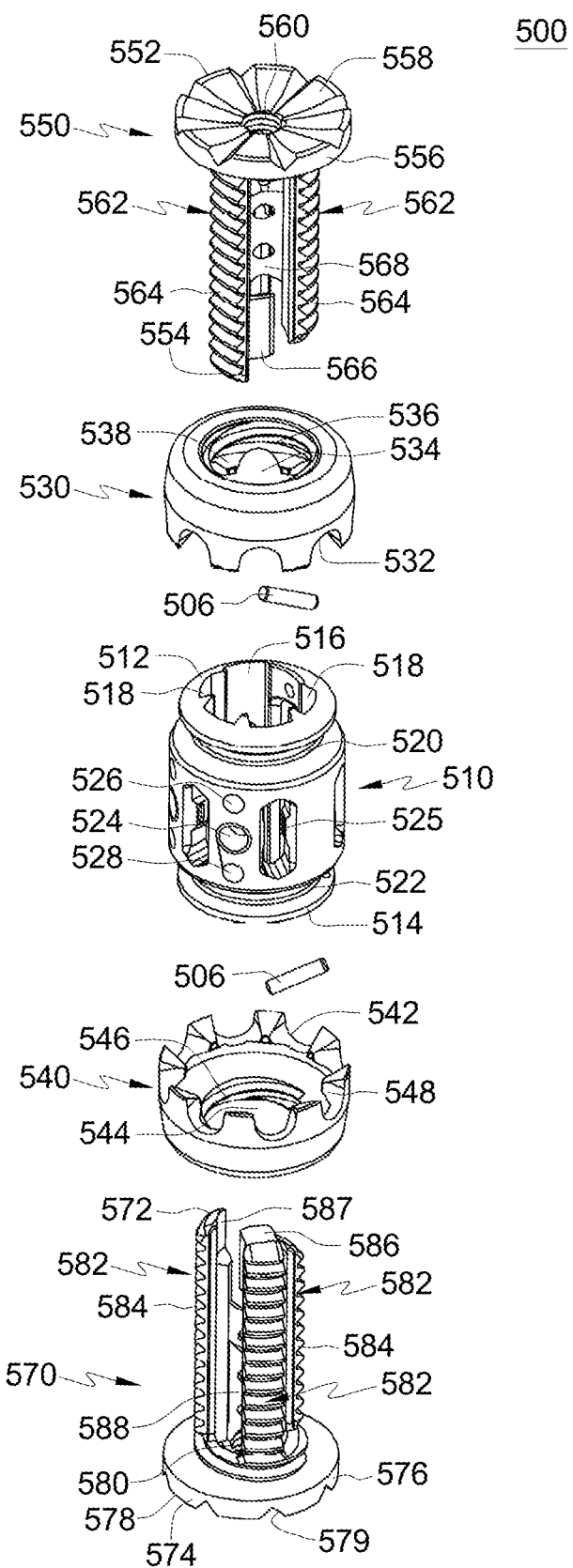
FIG. 5 is an exploded perspective view of the implant of FIG. 1, in accordance with an aspect of the present invention.
Figure 6:
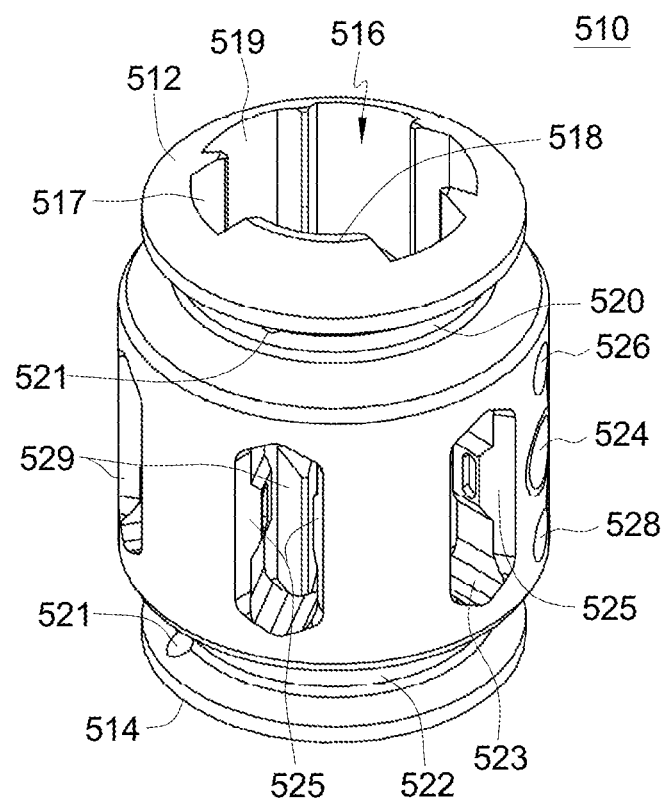
FIG. 6 is a top perspective view of a body of the vertebral body implant of FIG. 1, in accordance with an aspect of the present invention.
Figure 7:
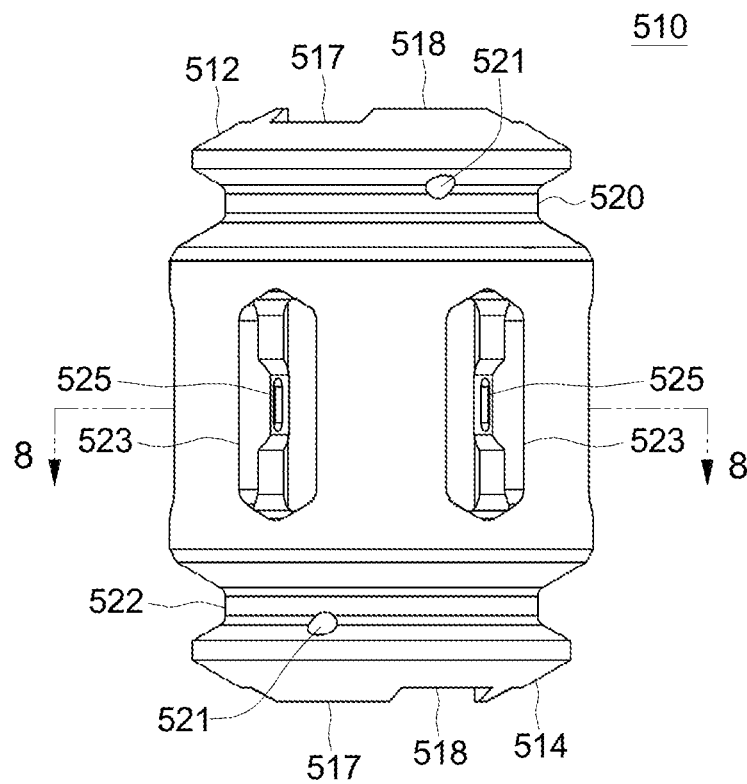
FIG. 7 is a side view of the body of FIG. 6, in accordance with an aspect of the present invention.
Figure 8:
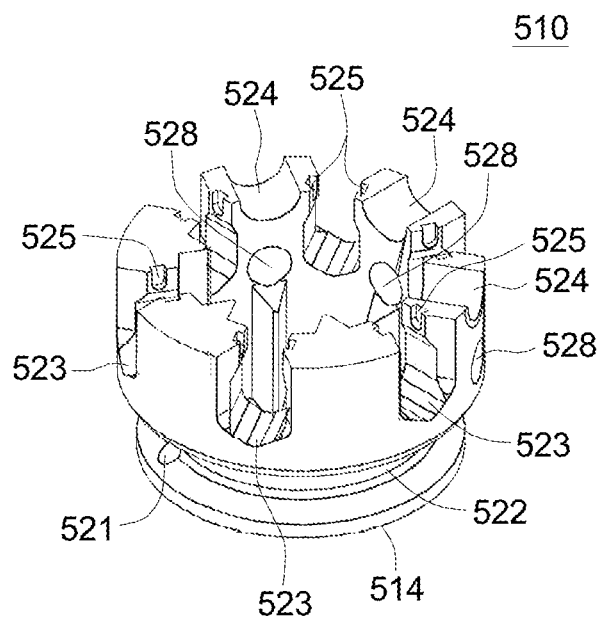
FIG. 8 is a perspective cross-sectional view of the body of FIG. 6 taken along line 8-8 in FIG. 7, in accordance with an aspect of the present invention.
Figure 9:
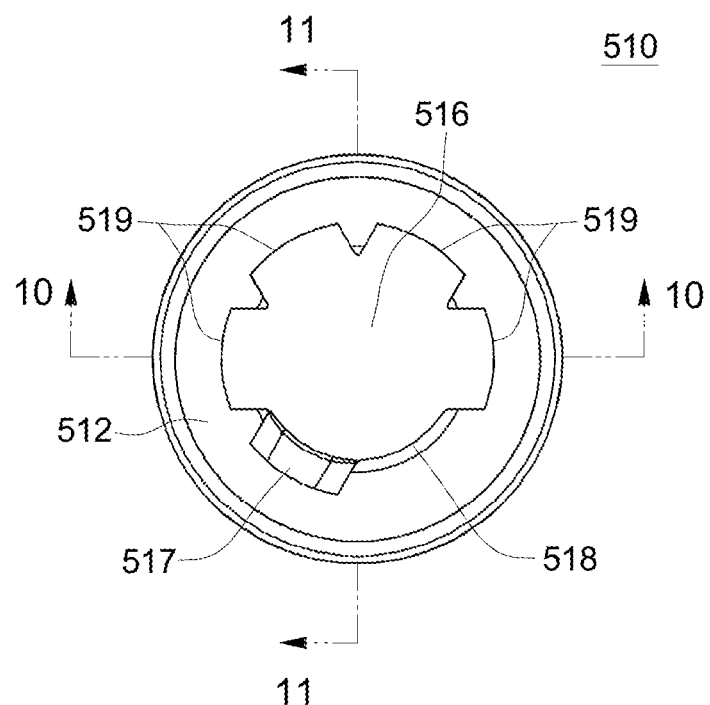
FIG. 9 is a top view of the body of FIG. 6, in accordance with an aspect of the present invention.
Figure 10:
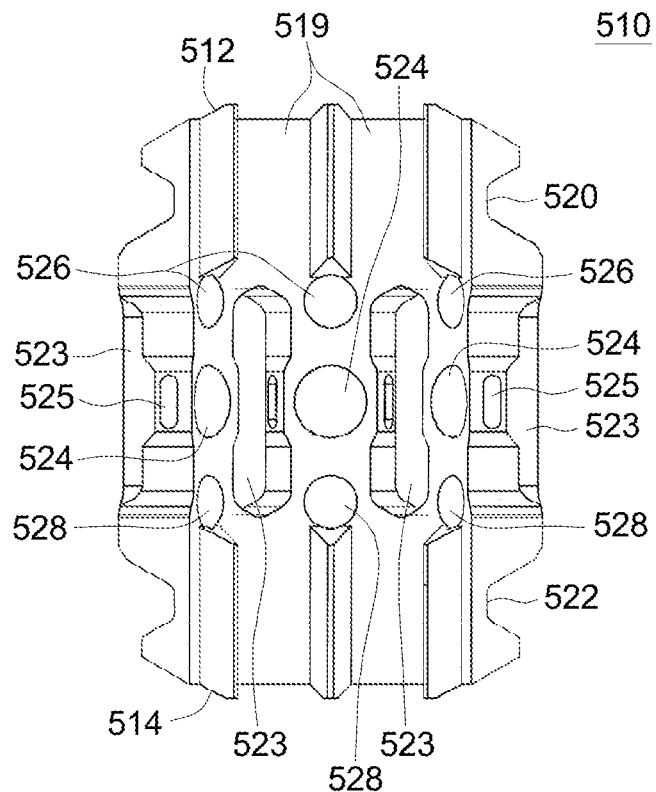
FIG. 10 is a cross-sectional view of the body of FIG. 6 taken along line 10-10 in FIG. 9, in accordance with an aspect of the present invention.
Figure 11:
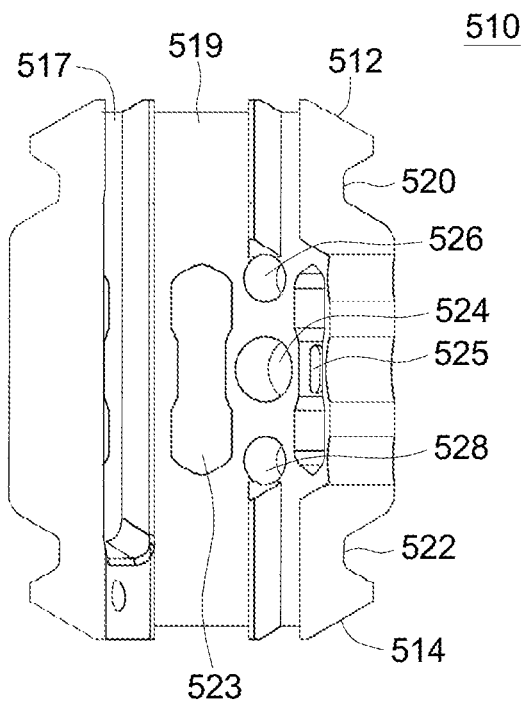
FIG. 11 is a cross-sectional view of the body of FIG. 6 taken along line 11-11 in FIG. 9, in accordance with an aspect of the present invention.
Figure 28:
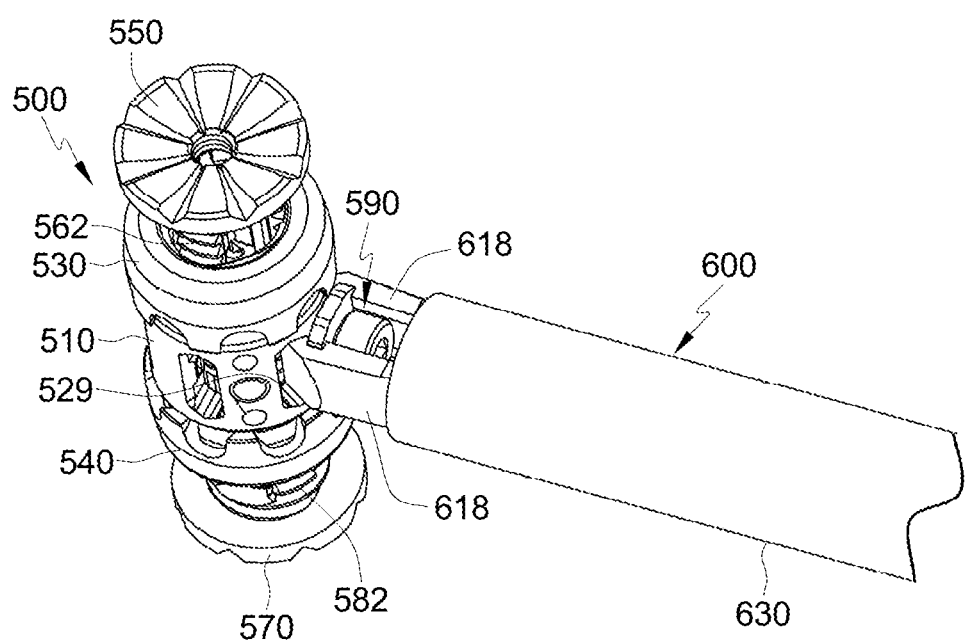
FIG. 28 is a top perspective view of the vertebral body implant of FIG. 1 in a second position and including a locking mechanism engaging the vertebral body implant of FIG. 1 and a portion of the insertion tool of FIG. 21, in accordance with an aspect of the present invention.
Figure 29:
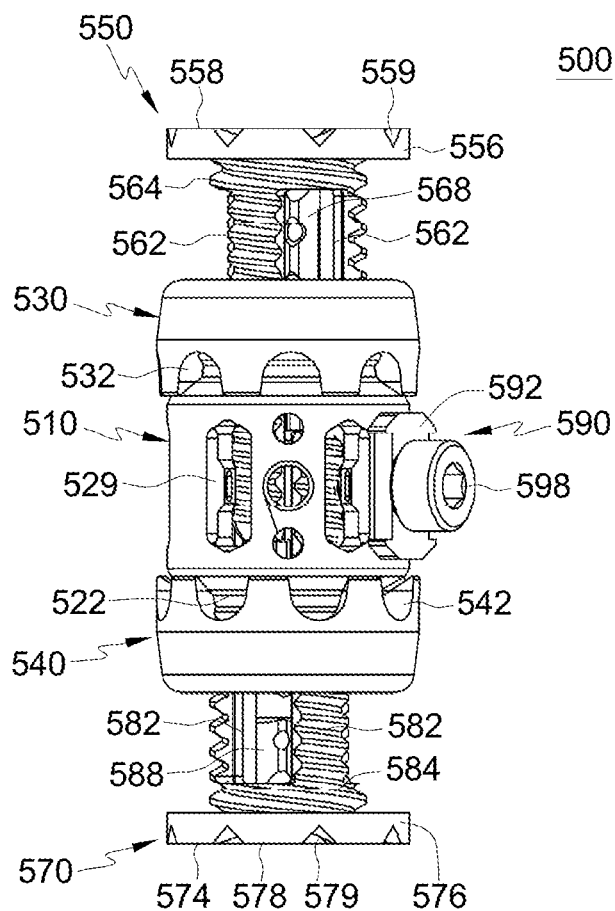
FIG. 29 is a side view of the vertebral body implant of FIG. 1 in an expanded position with the locking mechanism engaging at least a portion of the implant, in accordance with an aspect of the present invention.
Figure 30:
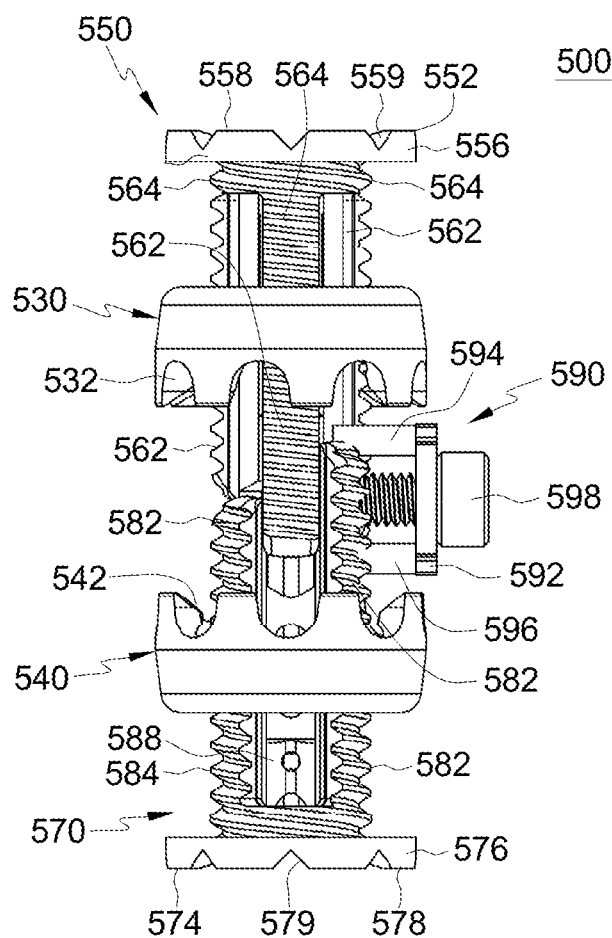
FIG. 30 is a side view of the vertebral body implant of FIG. 29 with the body of FIG. 6 removed, in accordance with an aspect of the present invention.
Figure 31:
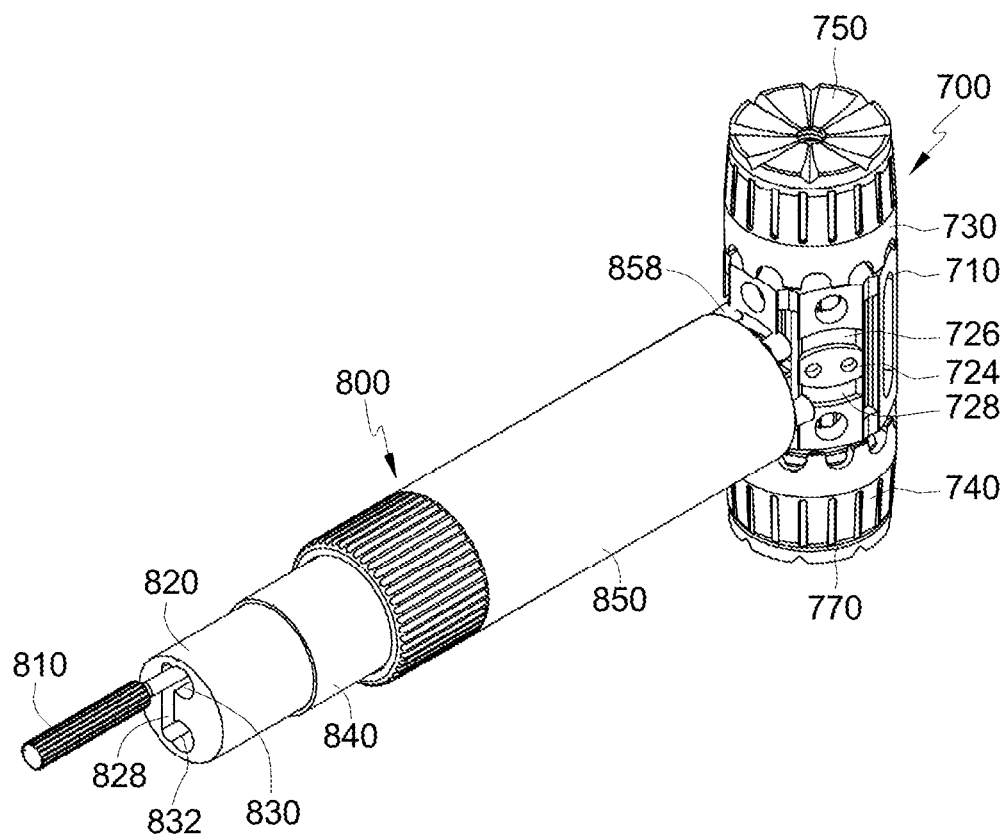
FIG. 31 is another embodiment of a vertebral body device system including a vertebral body implant and insertion tool, in accordance with an aspect of the present invention.

The exterior surface of the body 510 may further include a first groove 520 near the first end 512 and a second groove 522 near the second end 514, as shown in FIGS. 4-7. The first and second grooves 520, 522 may extend around the circumference of the body 510 and be sized to receive the first and second rotating members 530, 540, respectively. Each groove 520, 522 may include an opening 521 for receiving a pin 506. As shown in FIGS. 4-6, the body 510 may also include at least one aperture 524 positioned around the circumference of the exterior surface. The at least one aperture 524 may be positioned, for example, at a midpoint between the first end 512 and second end 514 of the body 510. The at least one aperture 524 may be, for example, a threaded opening. The body 510 may also include at least one first locking hole 526 superior to the aperture 524 and at least one second locking hole 528 inferior to the aperture 524. The aperture 524, first locking hole 526, and second locking hole 528 may be sized and shaped to receive a locking insert 590, as shown in FIGS. 28-30. In the depicted embodiment, the body 510 may include, for example, three apertures 524, three first locking holes 526, and three second locking holes 528. The three sets of openings 524, 526, 528 may be positioned adjacent to each other. The body 510 may further include openings 523 positioned around the circumference of the body 510. The openings 523 may each include at least one gripping surface or region 525 on each side of the opening 523 to couple to an insertion tool, such as, tool 600 described in greater detail below. As depicted, the three sets of openings 524, 526, 528 may be positioned between the openings 523 and adjacent to each other, such that, there are three solid portions of the body 510 positioned between the openings 523.

Figure 12:
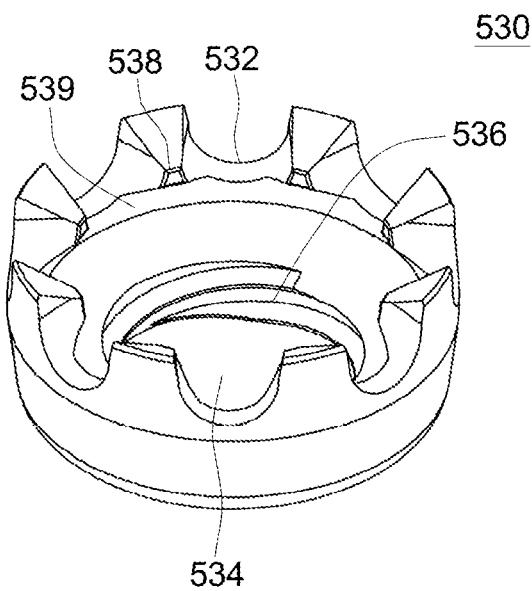
FIG. 12 is a perspective view of a rotating member of the vertebral body implant of FIG. 1, in accordance with an aspect of the present invention.
Figure 13:
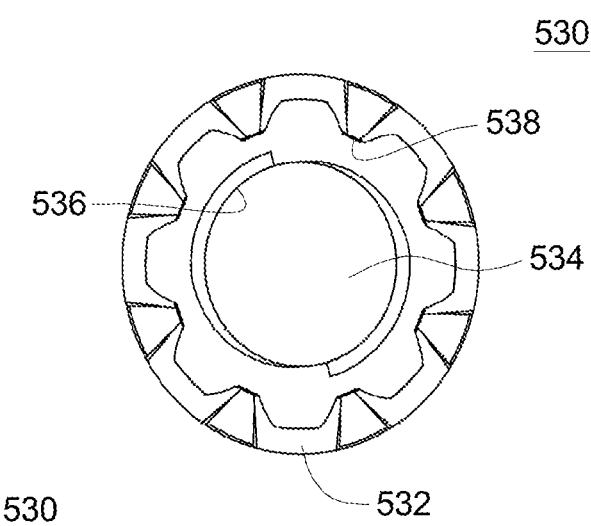
FIG. 13 is a first end view of the rotating member of FIG. 12, in accordance with an aspect of the present invention.
Figure 14:
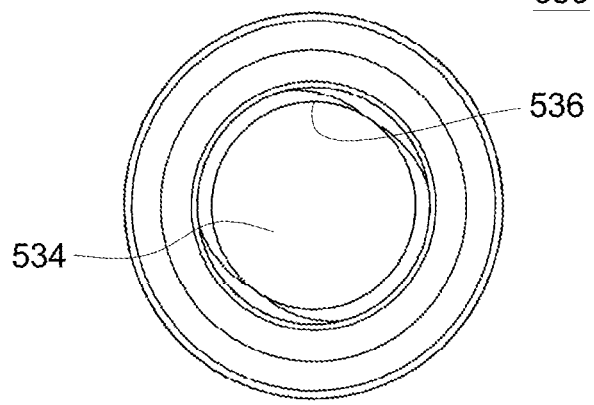
FIG. 14 is a second end view of the rotating member of FIG. 12, in accordance with an aspect of the present invention.

A rotating members 530, 540 are shown in FIGS. 4 and 5 and the rotating member 530 is shown in greater detail in FIGS. 12-14. The first rotating member 530 may include a center opening 534 extending through the first rotating member 530. The exterior surface of the first rotating member 530 may include a plurality of grooves, notches, gear teeth, teeth, or scallops 532, as best seen in FIGS. 12 and 13. The plurality of notches 532 may be, for example, sized to receive an insertion tool, such as tool 600 described in greater detail below. The first rotating member 530 may also include threads 536 on the interior surface of the member 530, as shown in FIGS. 5 and 12. In addition, the first rotating member 530 may include at least one protrusion 538 positioned between each notch 532 to engage the groove 520 in the body 510.

The second rotating member 540, as shown in FIGS. 4 and 5, may include a plurality of notches 542, a center opening 544, threads 546, and at least one protrusion 548. The plurality of notches 542, center opening 544, threads 546, and at least one protrusion 548 may be of the type described above with reference to the plurality of grooves 532, center opening 534, threads 536, and at least one protrusion 538 of first rotating member 530, which will not be described again here for brevity's sake.

Figure 15:
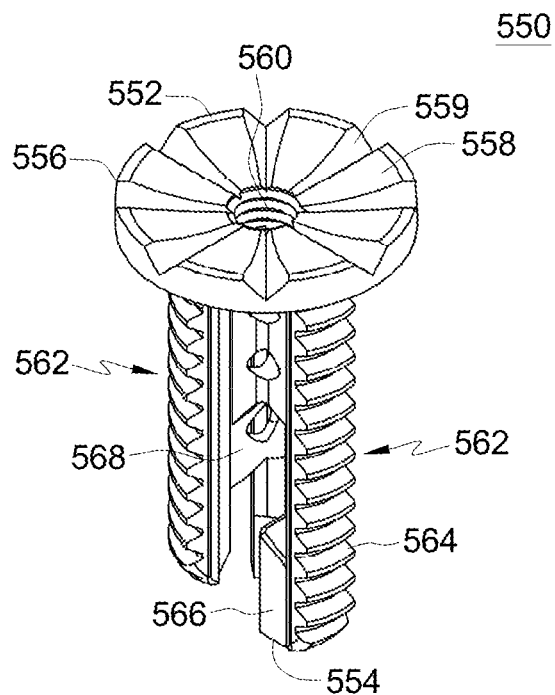
FIG. 15 is a first end perspective view of an extension member of the vertebral body implant of FIG. 1, in accordance with an aspect of the present invention.

Referring now to FIGS. 4 and 5, the extension members 550, 570 are shown. FIGS. 15-18 show the first extension member 550. The first extension member 550 may include a first end 552 and a second end 554. The first extension member 550 may also include a top portion or first end cap 556 at the first end 552 and at least one leg member 562 extending away from the top portion 556 and toward the second end 554. The top portion 556 may include a curved top surface 558, for example, a hemispherical or cylindrical shaped cup, and a center opening 560, as shown in FIGS. 5 and 15. The top surface 558 may also include grooves 559. The curved top surface 558, grooves 559, and center opening 560 may be configured to receive autologous bone graft or allograft material which will contact and allow for fusion with the adjacent vertebral bodies and additional graft material positioned between the at least one leg member 562. The curved surface 558 may be, for example, sized to allow the graft material to be positioned within the first extension member 550 to minimize the height. In addition, the hemispherical shaped cup may be selected, for example, to minimize the amount of graft material necessary to fill the curved surface 558. The top surface 558 may be, for example, coated, textured, porous, or of a trabecular metal nature to allow for bone growth into the first extension member 550 after implantation. In an alternative embodiment, it is also contemplated that the curved top surface 558 may be, for example, a mesh or open slotted top surface to allow for the bone graft material positioned in the top portion 556 to make contact with bone graft material positioned between the at least one leg member 562. The top portion 556 may also be configured to receive, for example, end caps (not shown) with lordosis or a larger footprint to contact larger adjacent vertebral bodies at the outer ring of their end plates.

Figure 16:
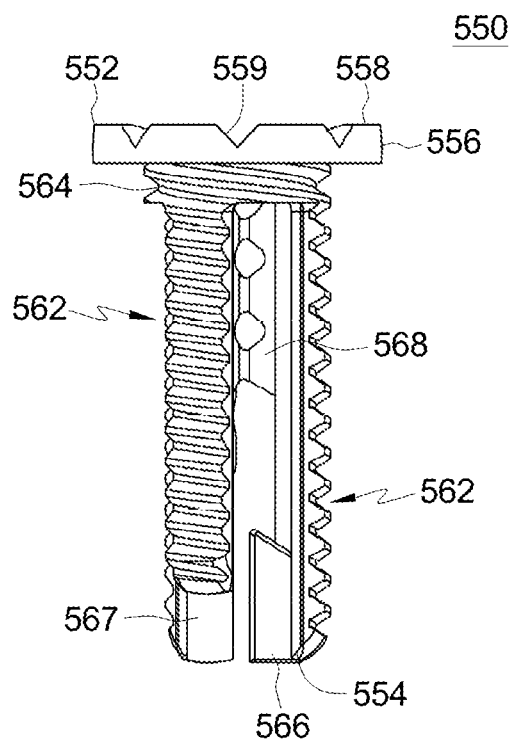
FIG. 16 is a side view of the extension member of FIG. 15, in accordance with an aspect of the present invention.
Figure 17:
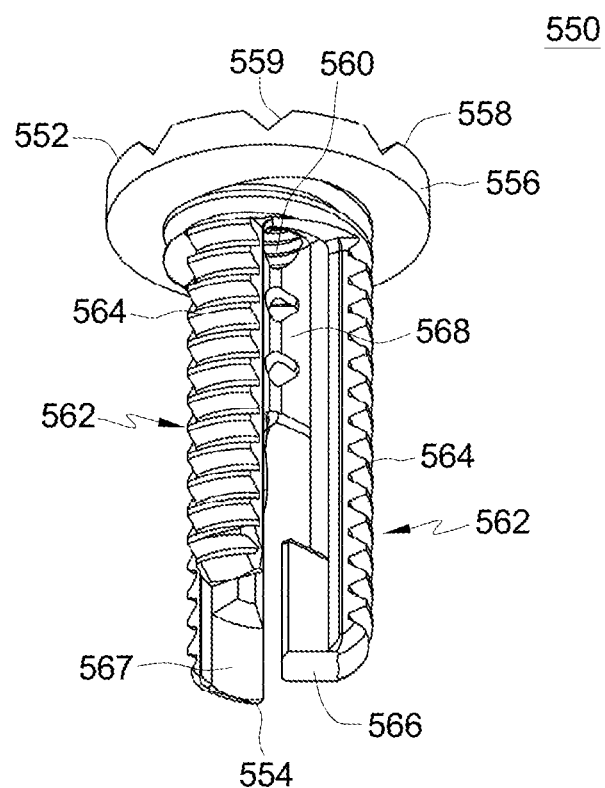
FIG. 17 is a second end perspective view of the extension member of FIG. 15, in accordance with an aspect of the present invention.
Figure 18:
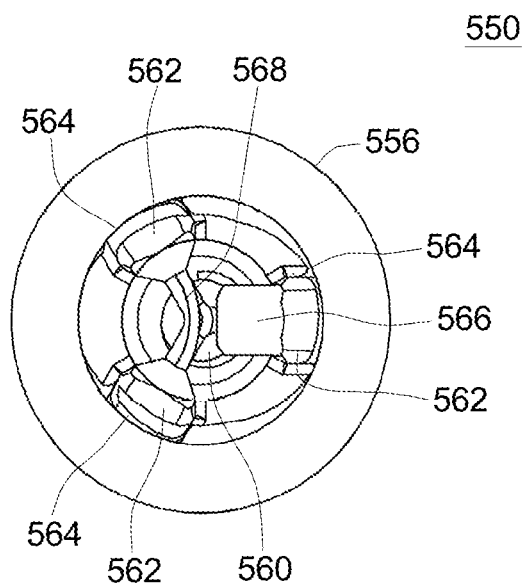
FIG. 18 is an end view of the extension member of FIG. 15, in accordance with an aspect of the present invention.

The at least one leg member 562 may be, for example, three leg members 562, as shown in FIGS. 15-18. The leg members 562 may include threads 564 on an exterior surface. The second end 554 of the leg members 562 may be, for example, tapered or angled. The leg members 562 may include a short leg member 562 and two longer leg members 562. The short leg member 562 may be received within the channel 517. A first longer leg member 562 may include a protrusion or hook 566 for engaging a channel 519 in the body 510. The protrusion 566 may include an angled end, as shown in FIG. 16, to engage at least one retention pin 506 during use. A second longer leg member 562 may include, for example, a recessed region 567. The threads 564 on the legs 562 engage the threads 536 on an interior surface of the first rotating member 530 to translate the leg member 562 with respect to the body 510. The threads 564 may extend from the second end 554 to a bottom surface of the first end cap 556. The leg members 562 may be curved to enable the leg members 562 to rotate with respect to the first rotating member 530. The first extension member 550 may also include support members 568 positioned between and connected to the leg members 562. The support members 568 may be, for example, cross-hatching braces positioned in rings. As depicted in FIGS. 15-18, the support members 568 may, for example, extend out from the back side of the leg members 562 and be connected between the leg members 562 in "Y" or "T" shaped arrangements. The support member 568 may also form an inner cylinder aligned with the opening 560 to form an inner channel through the implant 500. The arrangement of the leg members 562 may be, for example, curved between the leg members 562 to form a ring-like shape.

The second extension member 570, as shown in FIGS. 4 and 5, may include a first end 572 and a second end 574. The second extension member 570 may also include a bottom portion or second end cap 576 at the first end 572 and at least one leg member 582 extending away from the bottom portion 576 and to the second end 574. The bottom portion 576 may include a curved bottom surface 578 and an opening 580. The curved bottom surface 578 may be of the type described above with respect to the curved top surface 558, which will not be described again here for brevity's sake. The bottom surface 578 may also include grooves 579. The curved bottom surface 578, grooves 579, and center opening 580 may also be configured to receive autologous bone graft or allograft material as described in greater detail above with respect to the first extension member 550.

The at least one leg member 582 may be, for example, three leg members 582 and may include threads 584, protrusion or hook 586, and support members 588. The threads 584, protrusions 586, and support members 588 may be of the type described above with reference to threads 564, protrusion or hook 566, and support members 568, which will not be described again here for brevity's sake. The first end 572 of the leg members 582 may be, for example, tapered or angled. The leg members 582 may include a short leg member 582 and two longer leg members 582. The short leg member 582 may be received within the channel 518. A first longer leg member 582 may include a protrusion or hook 586 for engaging a channel 519 in the body 510. The protrusion 586 may include an angled end, as shown in FIG. 5, to engage at least one retention pin 506 during use. A second longer leg member 582 may include, for example, a recessed region 587. The threads 584 on the legs 582 engage the threads 546 on an interior surface of the second rotating member 540 to translate the leg member 582 with respect to the body 510. The threads 584 may extend from the first end 572 to a bottom surface of the second end cap 576. The leg members 582 may be curved to enable the leg members 582 to rotate with respect to the second rotating member 540. The first extension member 550 may also include support members 588 positioned between and connected to the leg members 582. The support members 588 may be, for example, cross-hatching braces positioned in rings. As depicted in FIGS. 15-18, the support members 588 may, for example, extend out from the back side of the leg members 582 and be connected between the leg members 582 in "Y" or "T" shaped arrangements. The support member 588 may also form an inner cylinder aligned with the opening 580 to form an inner channel through the implant 500. The arrangement of the leg members 582 may be, for example, curved between the leg members 582 to form a ring-like shape.

The implant 500 may also include a locking mechanism 590, as shown in FIGS. 28-30. The locking mechanism 590 may include a plate 592 with a first locking pin or post 594, a second locking pin or post 596 and an opening (not shown), for example, a threaded opening. The first locking post 594 is coupled to and extending away from the back surface of the plate 592. The second locking post 596 coupled to and extending away from the back surface of the plate 592. The locking posts 594, 596 are sized and shaped to engage the legs 562, 582 of the extension members 550, 570. The threaded opening (not shown) may be centered in the middle of the plate 592 and sized and shaped to receive a fastener 598 to lock the implant 500 in a desired position.

The vertebral body replacement device 500 may be assembled by obtaining a body 510 with a first rotating member 530 positioned in the first groove 520 and a second rotating member 540 positioned in the second groove 522. Next, the first and second extension members 550, 570 may be inserted into the channels 517, 518, 519 in the opening 516 of the body 510. The first extension member 550 may be inserted into the channels 517, 519 from the first end 512. During insertion into the channels 517, 519, the protrusion 566 of the first extension member 550 may be aligned with at least one channel 519 on the interior surface of the body 510. The first extension member 550 may be translated until the threads 564 of the leg members 562 engage the interior threads 536 of the first rotating member 530. The first rotating member 530 may be rotated until the first extension member 550 engages the first end 512 of the body 510. Once the first extension member 550 is positioned in the body 510, then, the second extension member 570 may be inserted into the opening 516. The second extension member 570 may be inserted into the channels 518, 519 from the second end 514. During insertion into the channels 518, 519, the protrusion 586 of the second extension member 570 may be aligned with at least one channel 519 on the interior surface of the body 510. The second rotating member 540 may be rotated until the second extension member 570 engages the second end 514 of the body 510. The locking plate may be coupled to the implant 500 using the aperture 524 and locking holes 526, 528. The fastener 598 may be partially screwed into place, so that the locking plate is coupled to the implant 500.

Figure 19:
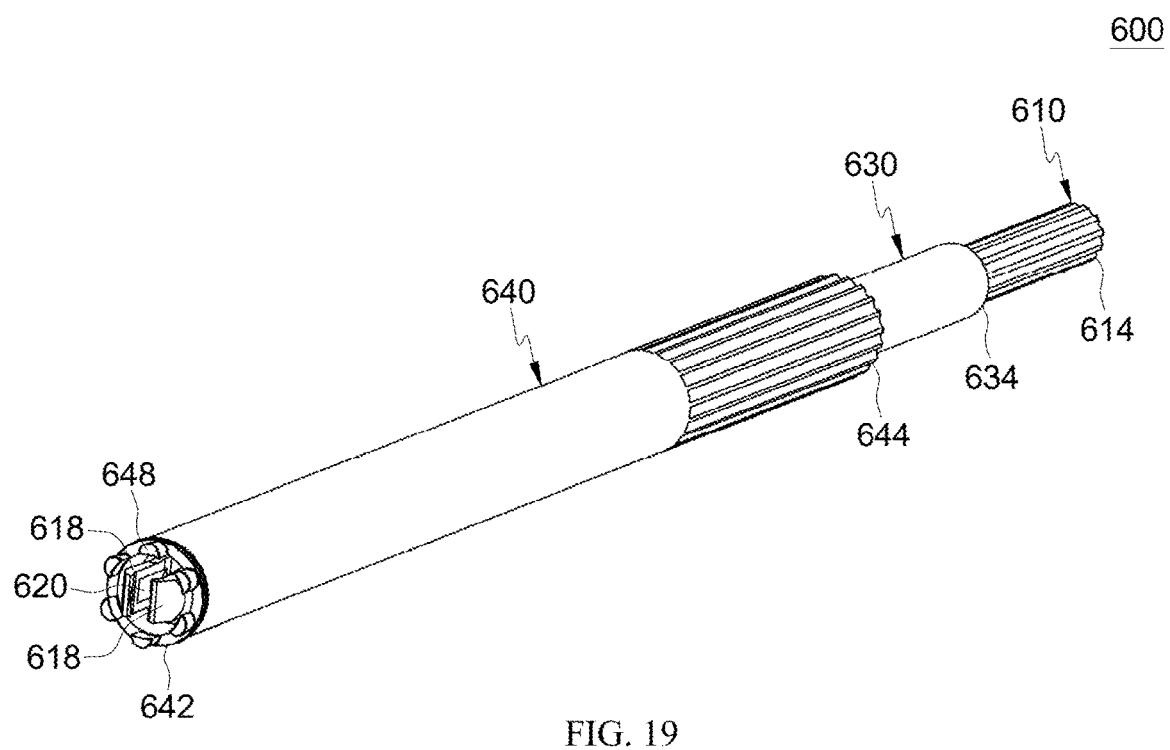
FIG. 19 is a perspective view of one embodiment of an insertion tool for the vertebral body implant of FIG. 1, in accordance with an aspect of the present invention.
Figure 20:
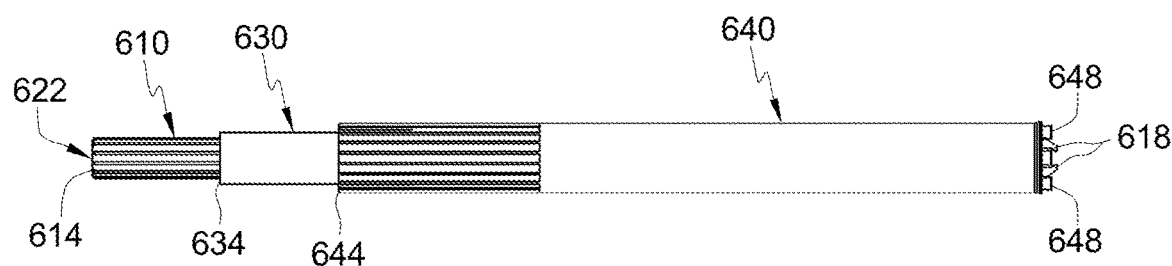
FIG. 20 is a side view of the insertion tool of FIG. 19, in accordance with an aspect of the present invention.
Figure 21:
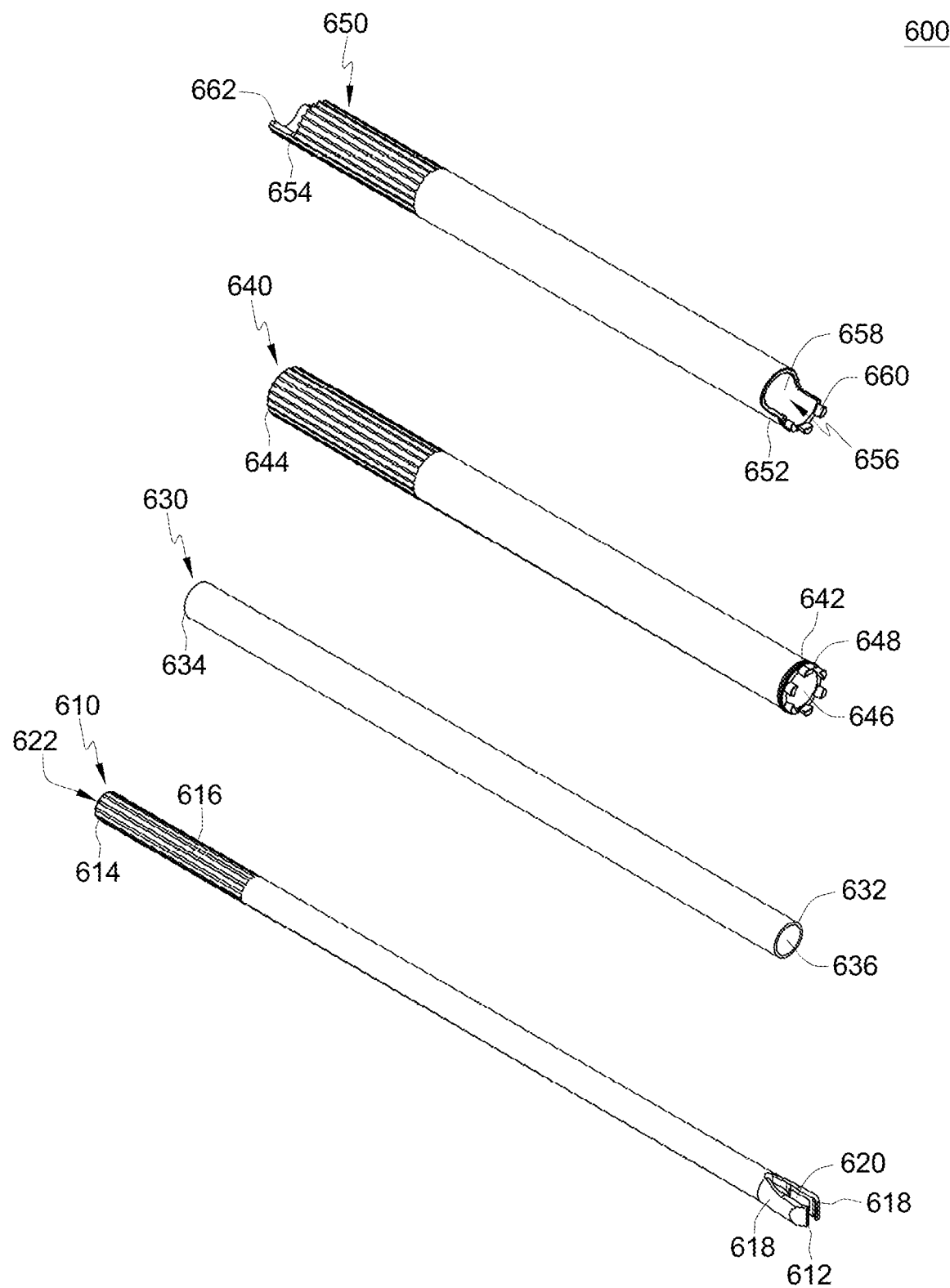
FIG. 21 is an exploded view of two embodiments of an insertion tool for the vertebral body implant of FIG. 1, in accordance with an aspect of the present invention.
Figure 22:
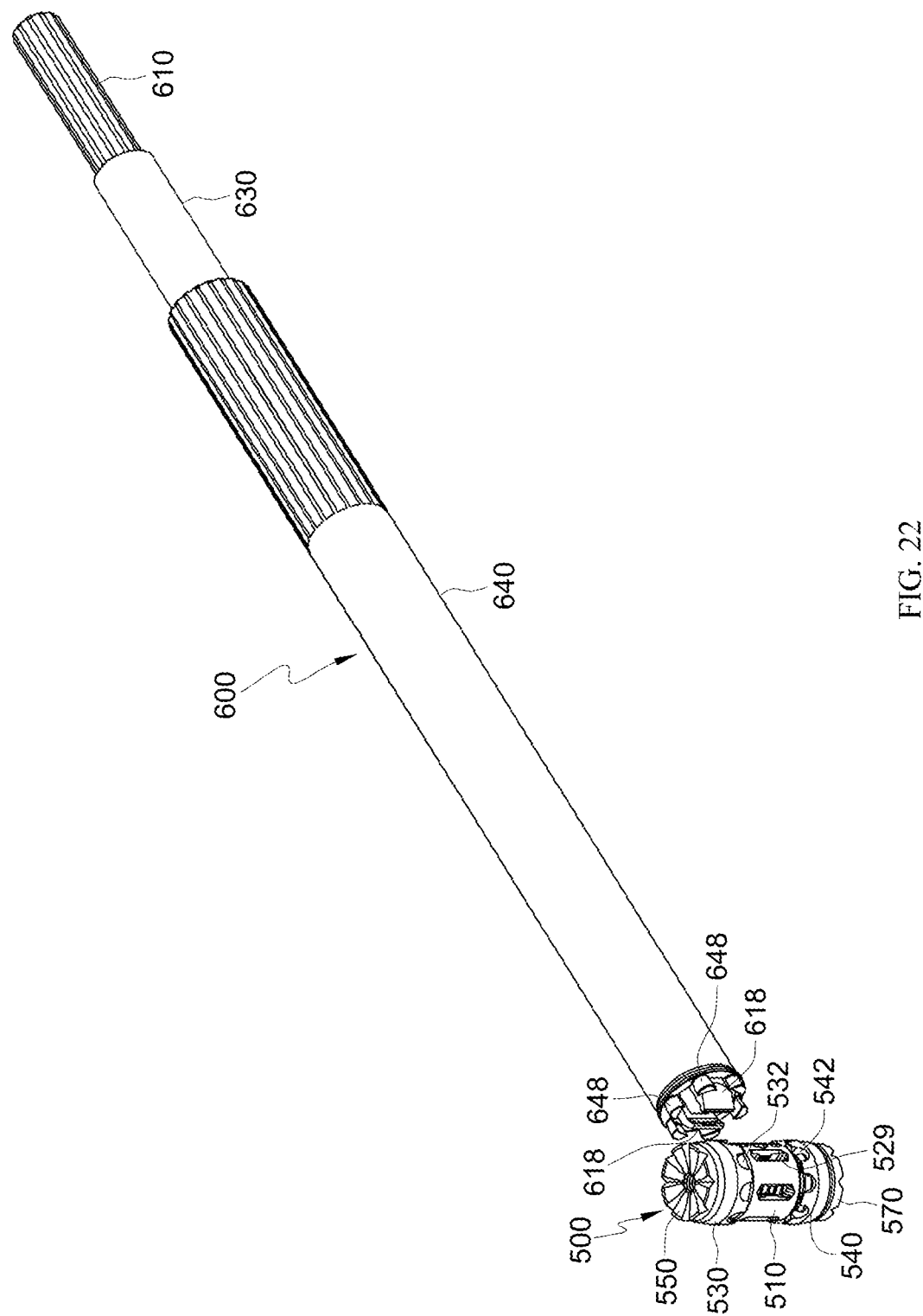
FIG. 22 is a perspective view of a vertebral body implant system including the implant of FIG. 1 and a first insertion tool of FIG. 19, in accordance with an aspect of the present invention.

An embodiment of an insertion tool 600 is shown in FIGS. 19-21. The insertion tool 600 may include a gripping member or tong member 610, a compression sleeve 630, a first deployment handle 640 and a second deployment handle 650. The gripping member 610 has a first end 612 and a second end 614 opposite the first end 612. The second end 614 may include a handle portion 616. The first end 612 may include two gripping arms 618 and each gripping arm 618 may include a channel 620 on an interior surface of the gripping arms 618. The gripping arms 618 sized and shaped to engage the gripping surfaces 525 on the body 510. The gripping arms 618 are also sized and shaped to grasp gripping surfaces 525 on body 510 while a locking member 590 is attached to or assembled to the body 510. The gripping arms 618 may be used to remove and reposition the locking member 590. The gripping member 610 may also include an opening extending along the longitudinal axis of the member 610 from the first end 612 to the second end 614. The compression sleeve 630 including a first end 632 and a second end 634 opposite the first end 632. The compression sleeve 630 also including an opening 636 extending from the first end 632 to the second end 634 and sized to receive the gripping member 610 and clamp the gripping arms 618 together to secure the implant 500 to the insertion tool 600.

As shown in FIGS. 19-25, the first deployment handle 640 includes a first end 642 and a second end 644 opposite the first end 642. The first deployment handle 640 also includes an opening 646 extending from the first end 642 to the second end 644. The first end 642 may also include a plurality of projections 648 sized and shaped to rotate the two rings 530 and 540 simultaneously to translate both extension members 550, 570 simultaneously. The plurality of projections 648 may be, for example, cone shaped or angled toward the point of attachment with the first end 642 of the handle 640 to allow for the projections 648 to engage the grooves or teeth 532, 542 of the rotating members 530, 540. The teeth 532, 542 may have, for example, an undercut or angled shape to lock the plurality of projections 648 into the teeth 532, 542 and prevent jumping of the projections 648 with respect to the teeth 532, 542 as the handle 610 is rotated.

Figure 26:
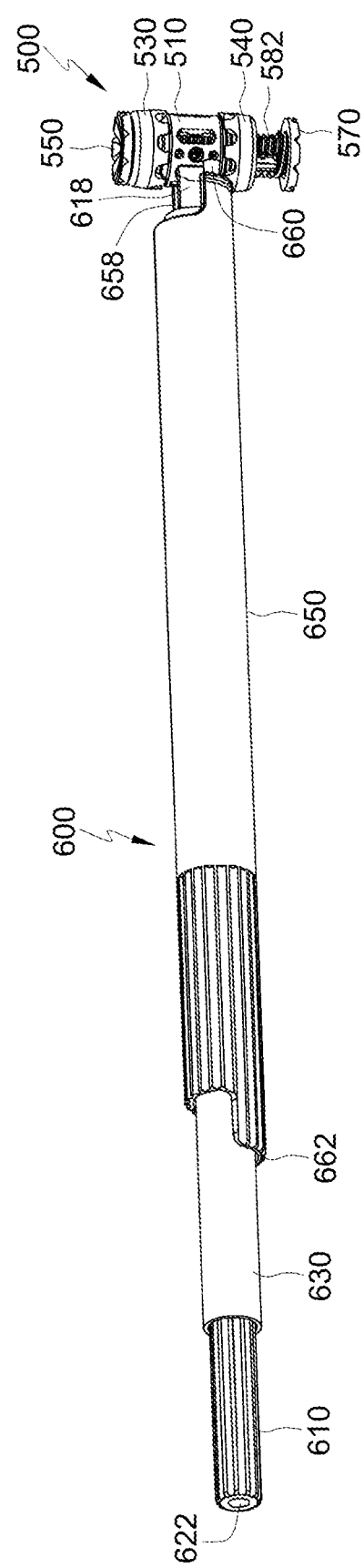
FIG. 26 is a perspective view of another embodiment vertebral body implant system including the implant of FIG. 1 and a second insertion tool in a first position, in accordance with an aspect of the present invention.
Figure 27:
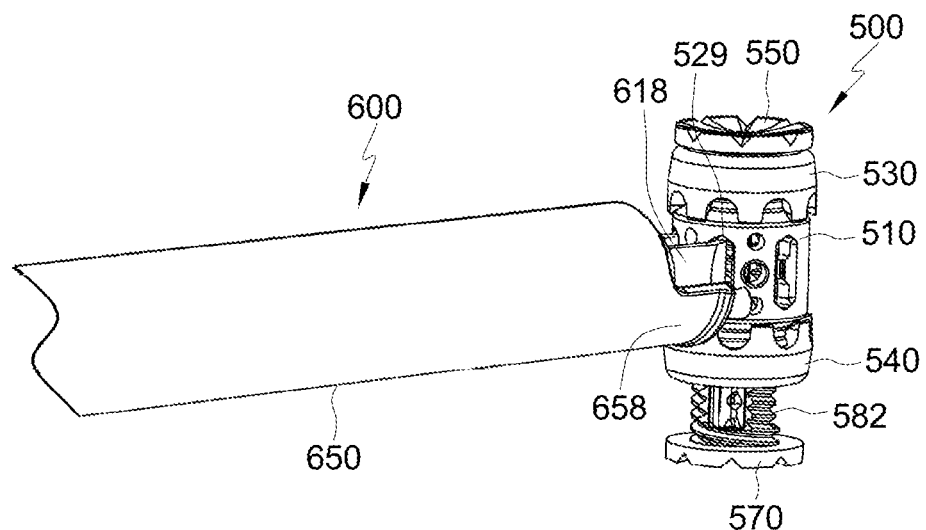
FIG. 27 is an enlarged perspective view of a portion of the system of FIG. 26, in accordance with an aspect of the present invention.

Referring now to FIGS. 21, 26, and 27, the second deployment handle 650 includes a first end 652 and a second end 654 opposite the first end 652. The second deployment handle 650 also including an opening 656 extending between the first end 652 and the second end 654. The first end 652 may also include a semi-circular protrusion 658 and the end of the protrusion 658 may include a plurality of projections 660. The plurality of projections 660 may be, for example, cone shaped or angled toward the point of attachment with the semi-circular protrusion 658 at the first end 652 of the handle 650 to allow for the projections 660 to engage the grooves or teeth 532, 542 of the rotating members 530, 540. The teeth 532, 542 may have, for example, an undercut or angled shape to lock the plurality of projections 660 into the teeth 532, 542 and prevent jumping of the projections 660 with respect to the teeth 532, 542 as the handle 650 is rotated. The second end 654 may also include a semi-circular protrusion 662 aligned with the semi-circular protrusion 658 on the first end 652.

Figure 23:
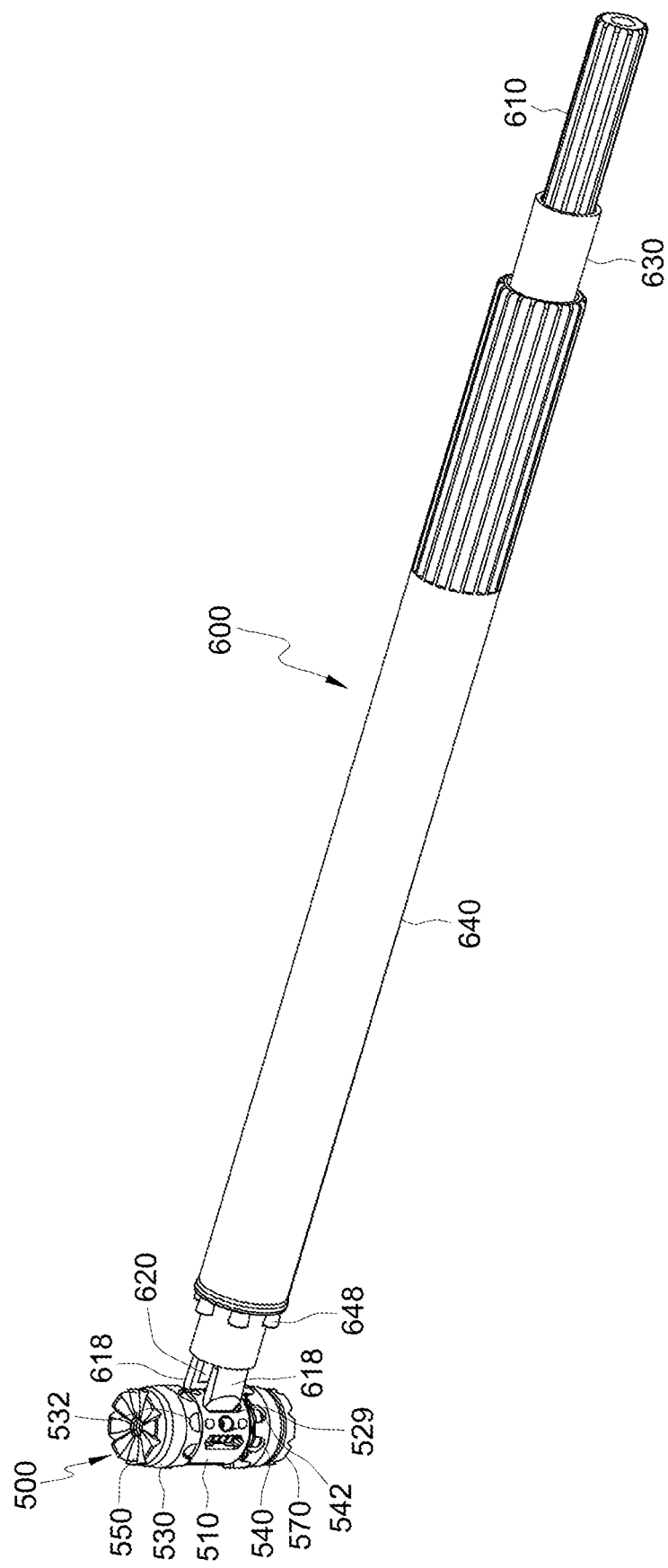
FIG. 23 is a perspective view of the vertebral body implant system of FIG. 22 with a tong member of the insertion tool engaging the vertebral body implant of FIG. 1, in accordance with an aspect of the present invention.
Figure 24:
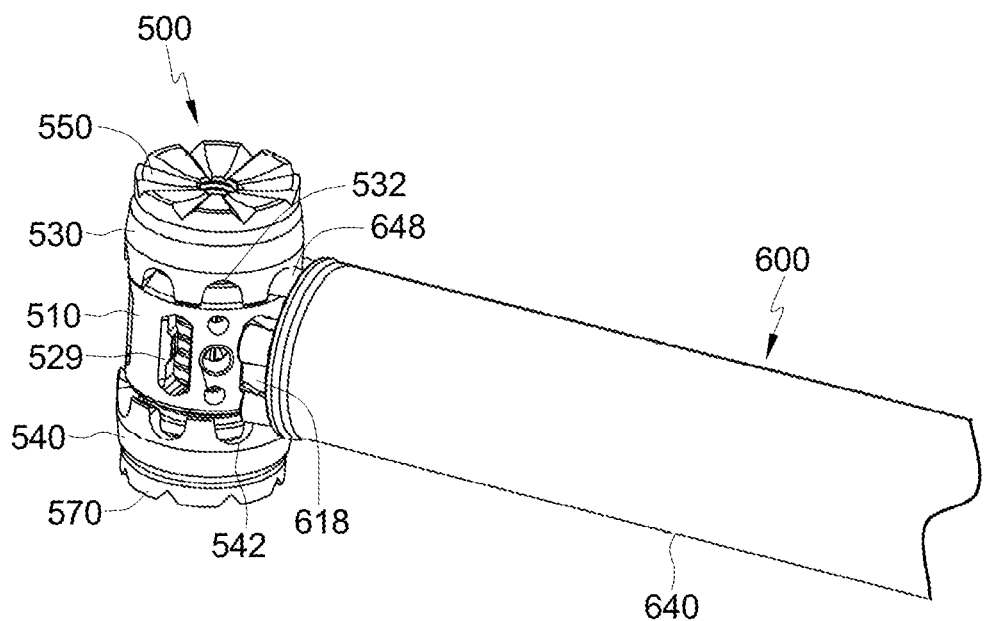
FIG. 24 is a perspective view of a portion of the system of FIG. 22 with the tool engaging the vertebral body implant in a first position, in accordance with an aspect of the present invention.
Figure 25:
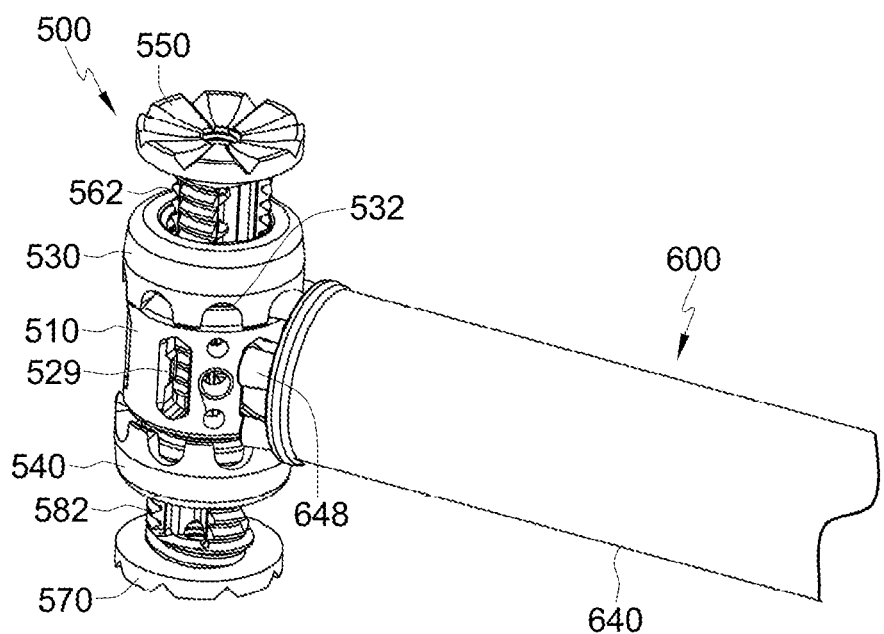
FIG. 25 is a perspective view of a portion of the system of FIG. 22 with the tool engaging the vertebral body implant in a second position, in accordance with an aspect of the present invention.

Referring now to FIGS. 22-30, methods of using the vertebral body implant 500 and insertion instruments 600 are shown. The method includes obtaining a vertebral body implant 500 and an insertion instrument 600. The vertebral body implant 500 and insertion instrument 600 may be assembled as described in greater detail above, which will not be described again here for brevity's sake. The instrument 600 may then be coupled to the vertebral body device 500 by inserting the gripping arms 618 of the gripping member 610 into the openings 523 to engage the gripping surfaces 525, as shown in FIG. 23. The gripping member 610 may be pre-loaded with a locking member 590 positioned between the gripping arms 618. The locking mechanism 590 may engage the aperture 524 and locking holes 526, 528 of the body 510.

Once the gripping member 610 is coupled to the implant 500, the compression sleeve 630 may be inserted over the gripping member 610. The compression sleeve 630 may engage the gripping member 610 to secure the gripping arms 618 to the implant 500 for insertion into the patient. Next, a deployment handle 640, 650 may be selected. If the surgeon wants to simultaneously extend both the expansion members 550, 570, then the first deployment handle 640 may be selected. Alternatively, if the surgeon wants to extend only one expansion member 550, 570 at a time, then the second deployment handle 650 may be selected.

After the deployment handle 640, 650 is selected it may be slid over the coupled gripping member 610 and compression sleeve 630. The plurality of projections 648, 660 of the selected deployment handle 640, 650 may be aligned with at least one set of the plurality of notches 532, 542 in at least one of the rotating members 530, 540. Once aligned the selected deployment handle 640, 650 may be rotated to turn at least one of the rotating members 530, 540. As at least one of the rotating members 530, 540 turns, at least one of the expansion members 550, 570 translates in a superior-inferior direction to expand the size of the implant 500. The first extension member 550 will translate in a superior direction increasing the height of the vertebral body implant 500. The second extension member 570 will translate in an inferior direction increasing the height of the vertebral body implant 500. The amount of superior-inferior translation is limited by the length of the leg members 562, 582. Alternatively, if the deployment handle 640, 650 is rotated in the reverse direction, at least one of the rotating members 530, 540 may be rotated in the reverse direction and at least one of the extension members 550, 570 will translate in the superior-inferior direction to decrease the height of the vertebral body implant 500. Once the desired configuration and height of the vertebral body implant 500 is achieved, the locking mechanism 590 may be tightened to lock the vertebral body implant 500 by inserting a driver through the insertion instrument 600. The locking mechanism 590 may be tightened with, for example, a hex wrench inserted through the center opening 524 of the instrument 600 to tighten the fastener 598 and secure the locking plate 592 in place on the implant 500. The locking mechanism 590 may engage the aperture 524 and locking holes 526, 528 of the body 510. Alternatively, the locking mechanism 590 may be inserted through the opening 622 in the gripping member 610 once the desired expansion is achieved. After the implant 500 is secured in the desired expanded position, the insertion tool 600 may be removed from the vertebral body implant 500.

Another embodiment vertebral body replacement device 700 and insertion instrument 800 are shown in FIGS. 31-34. The vertebral body device 700 may include a body 710, a first rotating member 730 rotatably coupled to the first end 712 of the body 710, a second rotating member 740 rotatably coupled to the second end 714 of the body 710, a first extension member 750 moveably coupled to the first end 712 of the body 710, and a second extension member 770 moveably coupled to a second end 714 of the body 710.

Figure 32:
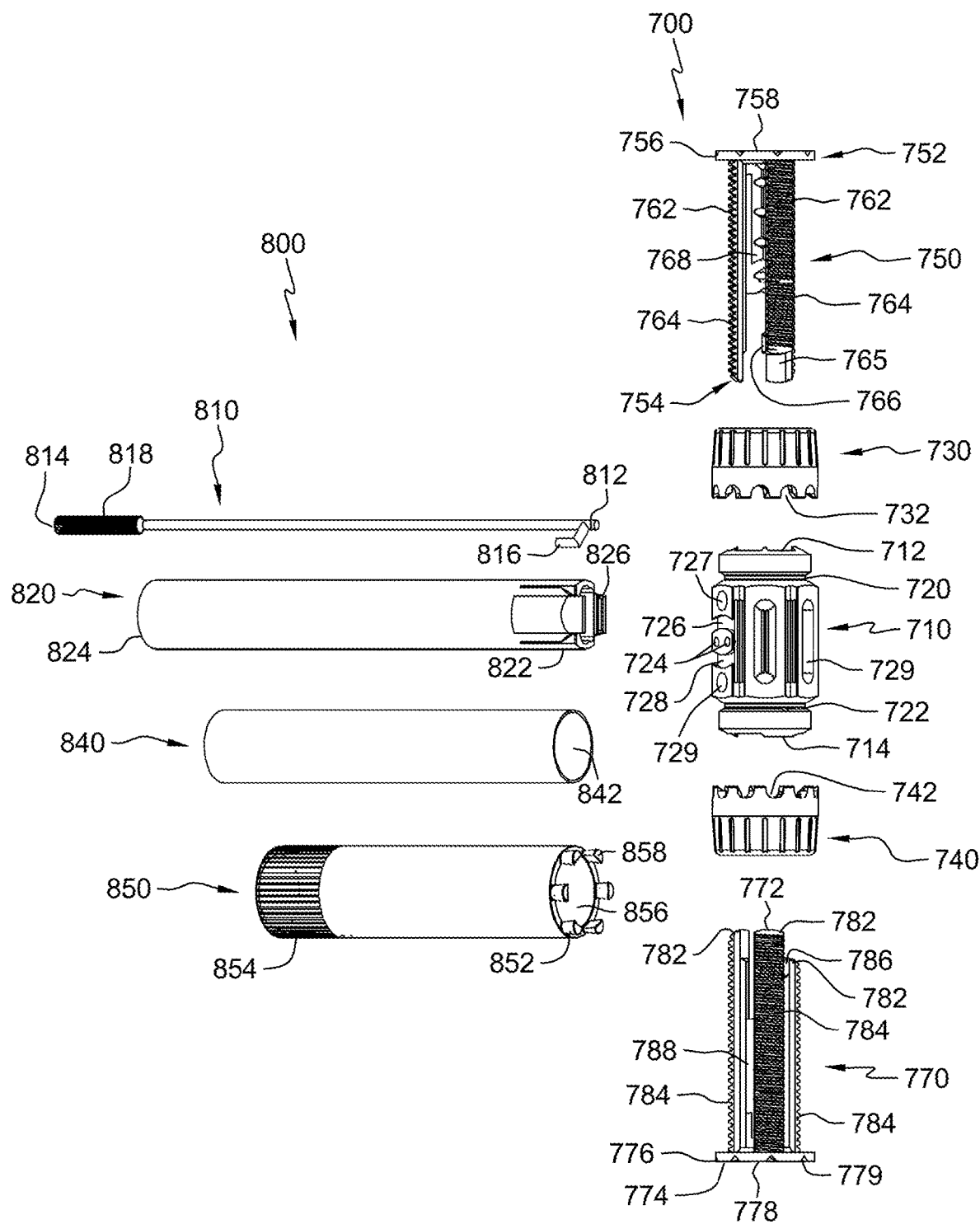
FIG. 32 is an exploded perspective view of the system of FIG. 31, in accordance with an aspect of the present invention.
Figure 34:
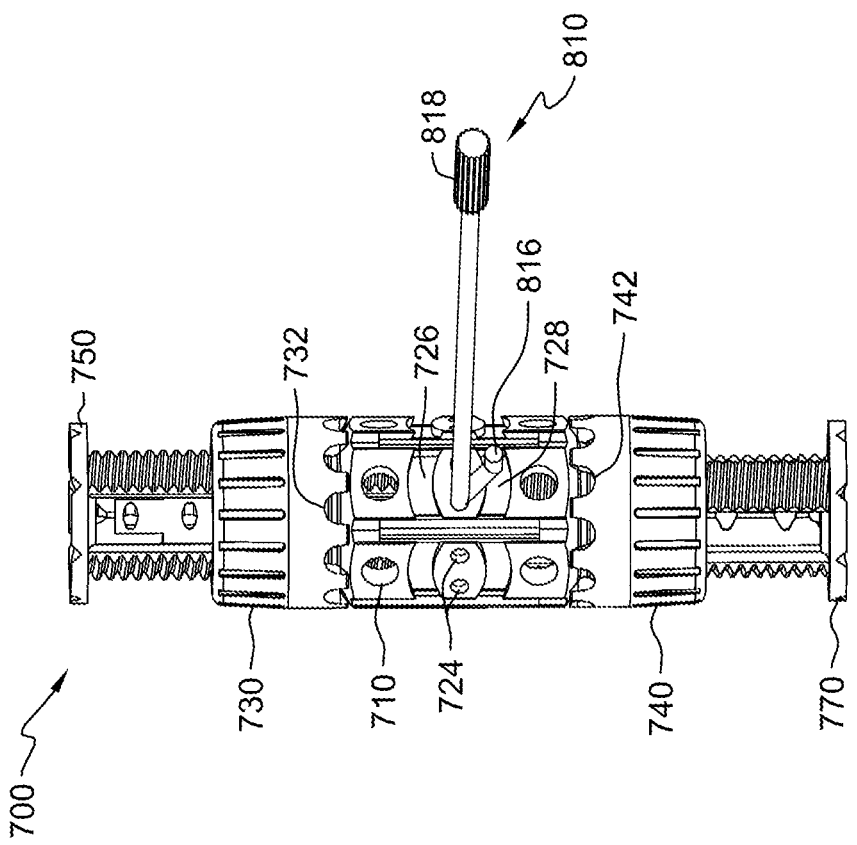
FIG. 34 is a side view of the system of FIG. 31 showing only a portion of the insertion tool, in accordance with an aspect of the present invention.

As shown in FIG. 32, the body 710 may include an opening (not shown) extending from the first end 712 to the second end 714, for example, along the longitudinal axis of the body 710. The opening (not shown) may include at least two channels (not shown) extending into the body 710 from the opening. The opening and channels may be of the type described above with reference to opening 516 and channels 517, 518, 519, which will not be described again here for brevity's sake. The exterior surface of the body 710 may further include a first groove 720 near the first end 712 and a second groove 722 near the second end 714, as shown in FIG. 32. The first and second grooves 720, 722 may extend around the circumference of the body 710 and be sized to receive the first and second rotating members 730, 740, respectively. As shown in FIGS. 32 and 34, the body 710 may also include at least one driver slot 726, 728 positioned on at least one section of the exterior surface. In one embodiment the driver slots 726, 728 may be located on three faces of the body 710 each spaced 60° apart from each other. The body 710 may also include at least one driver hole 724 positioned between the driver slots 726, 728. Further, the locking faces may include openings 727, 729 for receiving set screws (not shown) to secure the implant 700 in the desired expansion. The openings 727, 729 may be threaded. A first opening 727 may be positioned superior to the driver slots 726, 728 and the second opening 729 may be positioned inferior to the driver slots 726, 728. The body 710 may also include at least one opening 729 positioned on the non-locking faces. The at least one opening 729 may be sized and shaped to optimize bone grafting.

Figure 33:
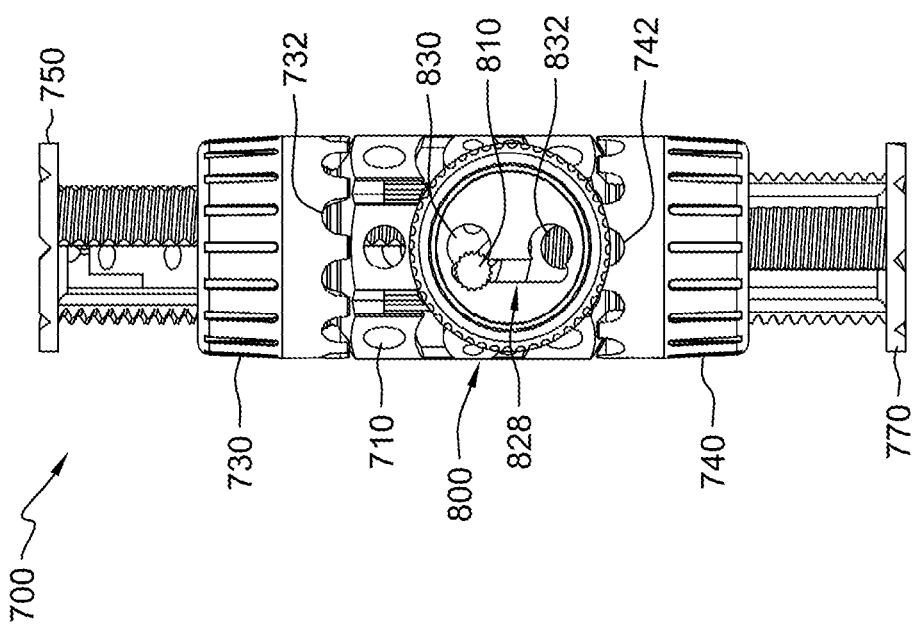
FIG. 33 is a side view of the implant of FIG. 31 and an end view of the insertion tool of FIG. 31, in accordance with an aspect of the present invention.

Rotating members 730, 740 are shown in FIG. 32 and the first rotating member 730 may include a center opening (not shown) extending through the first rotating member 730. The exterior surface of the first rotating member 730 may include a plurality of grooves, notches, gear teeth, teeth, or scallops 732, as best seen in FIGS. 32-34. The plurality of notches 732 may be, for example, sized to receive an insertion tool, such as tool 800 described in greater detail below. The first rotating member 730 may also include threads (not shown) on the interior surface of the member 730.

The second rotating member 740, as shown in FIG. 32, may include a plurality of notches 742, a center opening (not shown), and threads (not shown). The plurality of notches 542, center opening (not shown), and threads (not shown) may be of the type described above with reference to the plurality of grooves 732, center opening (not shown), and threads (not shown) of first rotating member 730, which will not be described again here for brevity's sake.

Referring now to FIG. 32, the extension members 750, 770 are shown. The first extension member 750 may include a first end 752 and a second end 754. The first extension member 750 may also include a top portion or first end cap 756 at the first end 752 and at least one leg member 762 extending away from the top portion 756 and toward the second end 754. The top portion 756 may include a top surface 758 and a center opening 760. The top surface 758 may also include grooves 759. The top surface 758, grooves 759, and center opening 760 may be configured to receive autologous bone graft or allograft material which will contact and allow for fusion with the adjacent vertebral bodies and additional graft material positioned between the at least one leg member 562. The surface 758 may be, for example, sized to allow the graft material to be positioned within the first extension member 750 to minimize the height. In addition, the top surface 758 may be shaped, for example, to receive graft material to allow for bone ingrowth to achieve the desired fusion. The top surface 758 may be, for example, coated, textured, porous, or of a trabecular metal nature to allow for bone growth into the first extension member 750 after implantation. In an alternative embodiment, it is also contemplated that the curved top surface 758 may be, for example, a mesh or open slotted top surface to allow for the bone graft material positioned in the top portion 756 to make contact with bone graft material positioned between the at least one leg member 762. The top portion 756 may also be configured to receive, for example, end caps (not shown) with lordosis or a larger footprint to contact larger adjacent vertebral bodies at the outer ring of their end plates.

The at least one leg member 762 may be, for example, three leg members 762, as shown in FIGS. 32-34. The leg members 762 may include threads 764 on an exterior surface. The leg members 762 may include a short leg member 762 and two longer leg members 762. The short leg member 762 may be received within a channel which does not extend the entire length of the body 710. In one embodiment, as shown in FIG. 32, the shorter leg member 762 may include a protrusion or hook 766 positioned on the distal portion of the leg member 762. The protrusion or hook 766 may be sized and shaped to engage a retention pin, for example, the protrusion 766 may include a proximal portion that is angled toward the leg member 762 creating a recess for receiving the retention pin. The longer leg members 762 may each be received within a channel which extends through the entire length of the body 710. The longer leg members 762 may each include, for example, a recessed region 765. In an alternative embodiment, for example, one of the longer leg members 762 may include the protrusion or hook 766 and the shorter leg member 762 and the second longer leg member 762 may each include a recessed region 765. The threads 764 on the legs 762 engage the threads 736 on an interior surface of the first rotating member 730 to translate the leg member 762 with respect to the body 710. The threads 764 may extend from the second end 754 to a bottom surface of the first end cap 756. The leg members 762 may be curved to enable the leg members 762 to rotate with respect to the first rotating member 730. The first extension member 750 may also include support members 768 positioned between and connected to the leg members 762. The support members 768 may be, for example, cross-hatching braces positioned in rings. As depicted in FIG. 32, the support members 768 may, for example, extend out from the back side of the leg members 762 and be connected between the leg members 762 in "Y" or "T" shaped arrangements. The support member 768 may alternatively form an inner cylinder aligned with the opening 760 to form an inner channel through the implant 700. The arrangement of the leg members 762 may be, for example, curved between the leg members 762 to form a ring-like shape.

The second extension member 770, as shown in FIG. 32, may include a first end 772 and a second end 774. The second extension member 770 may also include a bottom portion or second end cap 776 at the first end 772 and at least one leg member 782 extending away from the bottom portion 776 and to the second end 774. The bottom portion 776 may include a curved bottom surface 778 and an opening 780. The curved bottom surface 778 may be of the type described above with respect to the curved top surface 758, which will not be described again here for brevity's sake. The bottom surface 778 may also include grooves 779. The curved bottom surface 778, grooves 779, and center opening 780 may also be configured to receive autologous bone graft or allograft material as described in greater detail above with respect to the first extension member 750.

The at least one leg member 782 may be, for example, three leg members 782 and may include threads 784, protrusion or hook 786, and support members 788. The threads 784, protrusions 786, and support members 788 may be of the type described above with reference to threads 764, protrusion or hook 766, and support members 768, which will not be described again here for brevity's sake. The leg members 782 may include a short leg member 782 and two longer leg members 782. The short leg member 782 may be received within a channel which extends along a portion of the length of the body 710. A first longer leg member 782 may include a protrusion or hook 786 for engaging a channel 719 in the body 710. A second longer leg member 782 may include, for example, a recessed region 787. The threads 784 on the legs 782 engage the threads 746 on an interior surface of the second rotating member 740 to translate the leg member 782 with respect to the body 710. The threads 784 may extend from the first end 772 to a bottom surface of the second end cap 776. The leg members 782 may be curved to enable the leg members 782 to rotate with respect to the second rotating member 740. The first extension member 750 may also include support members 788 positioned between and connected to the leg members 782. The support members 788 may be, for example, cross-hatching braces positioned in rings. As depicted in FIG. 32, the support members 788 may, for example, extend out from the back side of the leg members 782 and be connected between the leg members 782 in "Y" or "T" shaped arrangements. The support member 788 may alternatively form an inner cylinder aligned with the opening 780 to form an inner channel through the implant 700. The arrangement of the leg members 782 may be, for example, curved between the leg members 782 to form a ring-like shape.

As shown in FIGS. 32-33, the insertion instrument 800 may include shifter 810, a gripper member 820, a locking sleeve 840, and a driver sleeve 850. The shifter 810 includes a first end 812, a second end 814, an extension member 816 and a handle 818. The gripper member 820 includes a first end 822, a second end 824 and an opening 828, 830, 832 extending between the first end 822 and the second end 824. The gripper member 820 may also include at least two gripper arms 826 sized and shaped to engage the body 710 of the implant 700. The opening 828, 830, 832 may include a slot 828 extending in a superior-inferior direction, a first opening 830 positioned at the superior end of the slot 828 and a second opening 832 positioned at the inferior end of the slot 828. The opening 828, 830, 832 may be shaped to receive the shifter 810.

With continued reference to FIG. 32, the locking sleeve 840 may include an opening 842 extending from a first end to a second end of the locking sleeve 840. The opening 842 may be sized and shaped to receive the gripper member 820 to secure the gripping arms 826 to the implant 700. The drive sleeve 850 may include a first end 852 and a second end 854. The driver sleeve 850 may also include an opening 856 extending from the first end 852 to the second end 854 and a plurality of projections, protrusions, teeth, or gear members 858 for engaging the rotating members 730, 740. The plurality of projections 858 may be, for example, cone shaped or angled toward the point of attachment with the first end of the drive sleeve 850 to allow for the projections 858 to engage the grooves or teeth 732, 742 of the rotating members 730, 740. The teeth 732, 742 may have, for example, an undercut or angled shape to lock the plurality of projections 858 into the teeth 732, 742 and prevent jumping of the projections 858 with respect to the teeth 732, 742 as the drive sleeve 850 is rotated.

Referring now to FIGS. 33-34, the extension member 816 of the shifter 810 engages the slots 726, 728 to move the driver sleeve 850 from engagement with the first rotating member 730 to the second rotating member 740 and vice versa. The shifter 810 may be positioned in the first opening 830 to engage the second rotating member 740, as shown in FIG. 33, and in the second opening 832 to engage the first rotating member 730. Once an extension member 750, 770 is positioned at the desired extension a set screw may be inserted into the respective opening 727, 729 to secure the extended extension member 750, 770. After one extension member 750, 770 is expanded and secured, the second extension member 750, 770 may be extended and secured.

FIGS. 35-36 show another embodiment of a vertebral body replacement implant 900. The implant 900 may include a body 910, a first rotating member 930 rotatably coupled to the first end 912 of the body 910, a second rotating member 940 rotatably coupled to the second end 914 of the body 910, a first extension member 950 moveably coupled to the first end 912 of the body 910, and a second extension member 970 moveably coupled to a second end 914 of the body 910. The body may include a first end 912 and a second end 914. As shown in FIG. 36, the body 910 may include a first angled opening 916 and a second angled opening 918. The angled openings 916, 918 may be, for example, threaded openings. The first angled opening 916 may extend in a superior direction and the second angled opening 918 may extend in an inferior direction. The first rotating member 930 and the second rotating member 940 may be of the type described above with reference to rotating members 730, 740 and which will not be described again here for brevity's sake. The first extension member 950 and second extension member 970 may be of the type described above with reference to extension members 750, 770 and which will not be described again here for brevity's sake.

Figure 37:
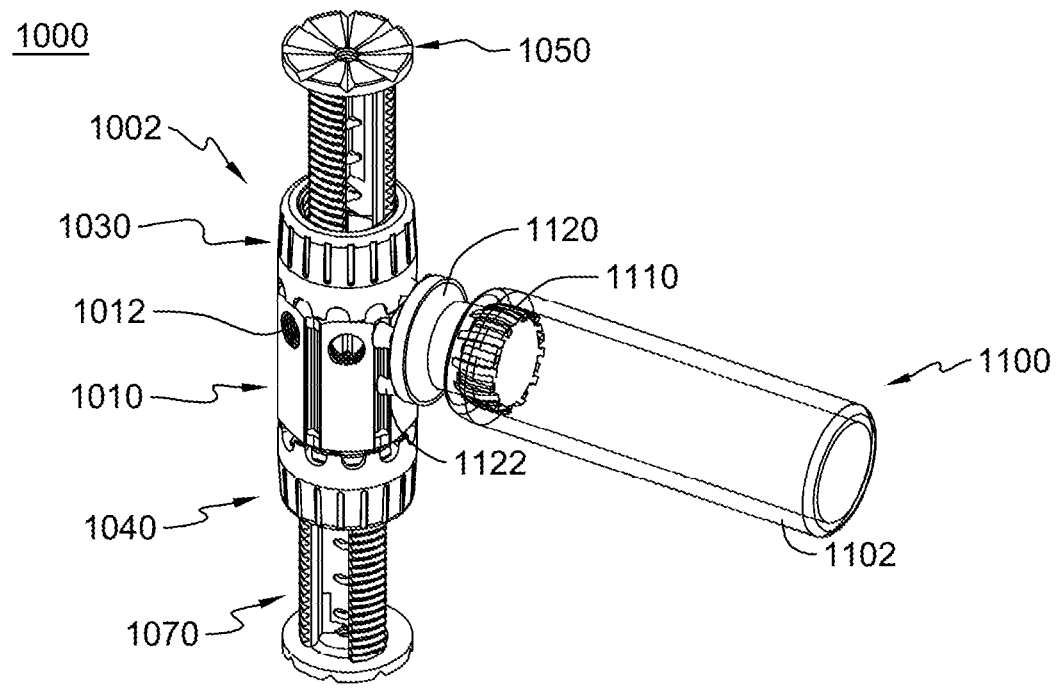
FIG. 37 is another embodiment of a vertebral body system including an implant and insertion instrument, in accordance with an aspect of the present invention.
Figure 38:
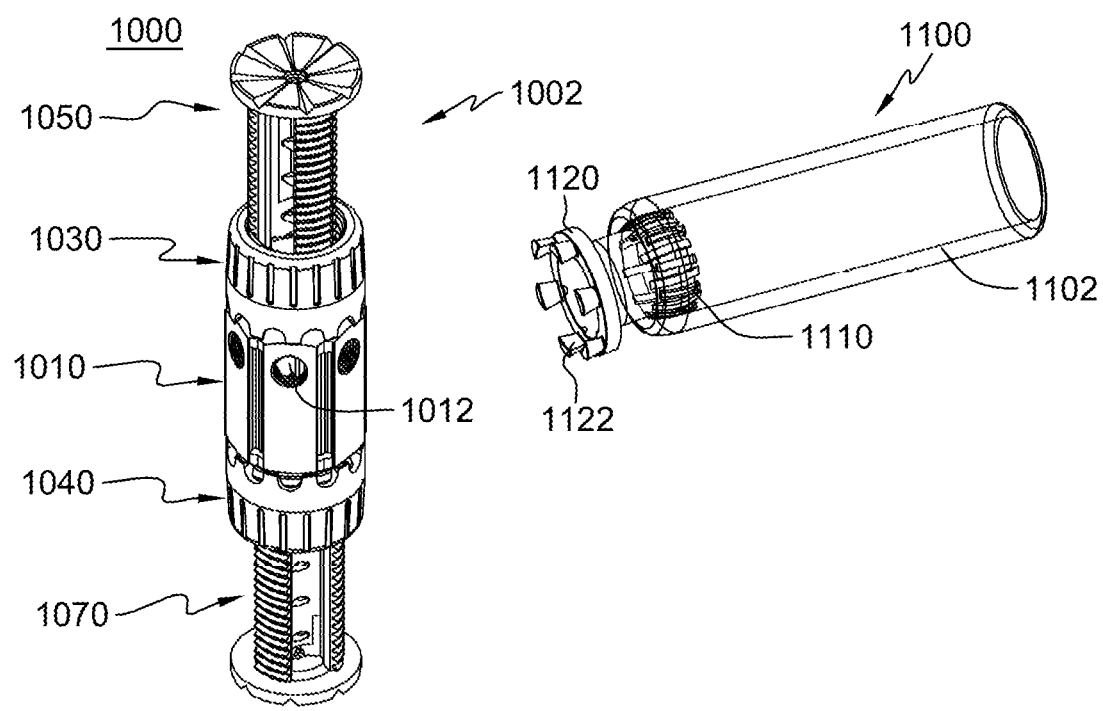
FIG. 38 is a partially exploded view of the vertebral body system of FIG. 37, in accordance with an aspect of the present invention.

Another embodiment vertebral body replacement system 1000 is shown in FIGS. 37-38. The system 1000 includes an implant 1002 and a driver sleeve 1100. The implant 1002 may include a body 1010, a first rotating member 1030 rotatably coupled to the first end 1012 of the body 1010, a second rotating member 1040 rotatably coupled to the second end 1014 of the body 1010, a first extension member 1050 moveably coupled to the first end 1012 of the body 1010, and a second extension member 1070 moveably coupled to a second end 1014 of the body 1010. The body may include a first end 1012 and a second end 1014. As shown in FIGS. 37-38, the body 1010 may include at least one opening 1012. The openings 1012 may be, for example, threaded openings. The first rotating member 1030 and the second rotating member 1040 may be of the type described above with reference to rotating members 730, 740, 930, 940 and which will not be described again here for brevity's sake. The first extension member 1050 and second extension member 1070 may be of the type described above with reference to extension members 750, 770, 950, 970 and which will not be described again here for brevity's sake.

The driver sleeve 1100 may include a body 1102 and a driver head 1120 at a first end of the body 1102. The driver head 1120 may include a pivoting member 1110 coupled to the body 1102 and a plurality of projections, protrusions, teeth, gear members 1122 for engaging the rotating members 1030, 1040. The plurality of projections 1122 may be, for example, cone shaped or angled toward the point of attachment with the first end of the driver head 1120 to allow for the projections 1122 to engage the grooves or teeth 1032, 1042 of the rotating members 1030, 1040. The teeth 1032, 1042 may have, for example, an undercut or angled shape to lock the plurality of projections 1122 into the teeth 1032, 1042 and prevent jumping of the projections 1122 with respect to the teeth 1032, 1042 as the driver head 1120 and body 1102 are rotated. The pivoting member 1110 may be, for example, a splined end that allows for the driver 1100 to pivot at an angle while being rotated to turn the rotating members 1030, 1040.

Figure 39:
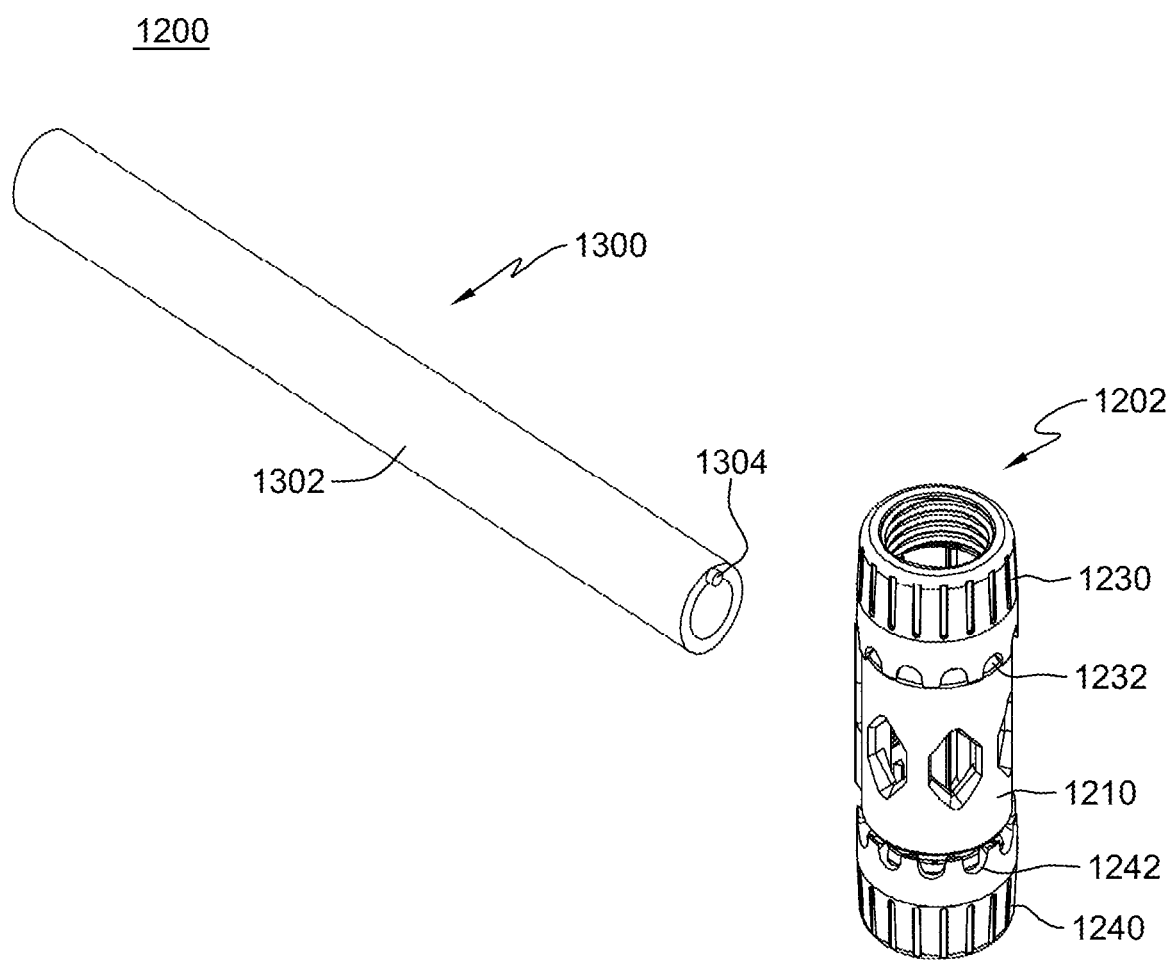
FIG. 39 is a perspective partially exploded view of another embodiment vertebral body system including an implant and an insertion instrument, in accordance with an aspect of the present invention.
Figure 40:
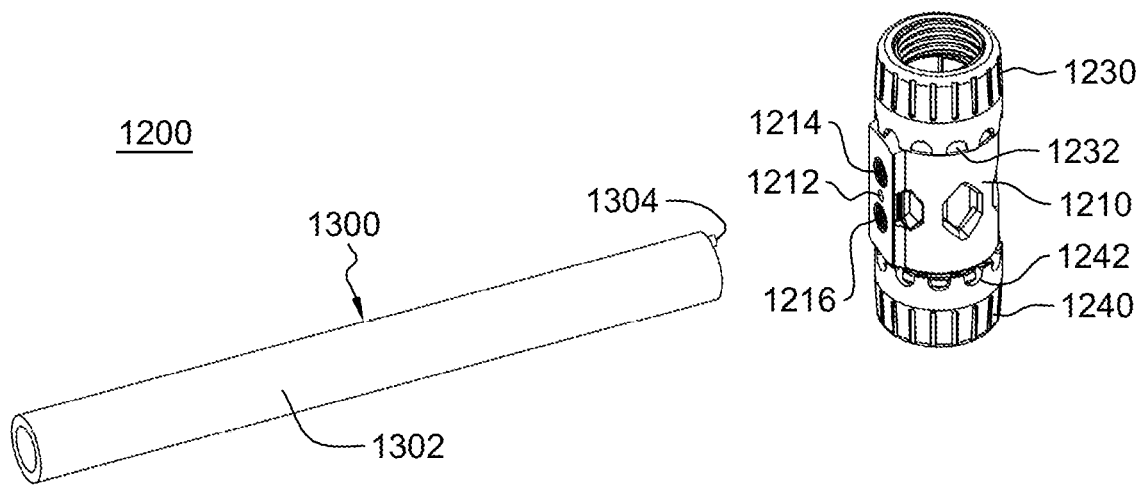
FIG. 40 is another perspective partially exploded view of the vertebral body system of FIG. 39, in accordance with an aspect of the present invention.
Figure 41:
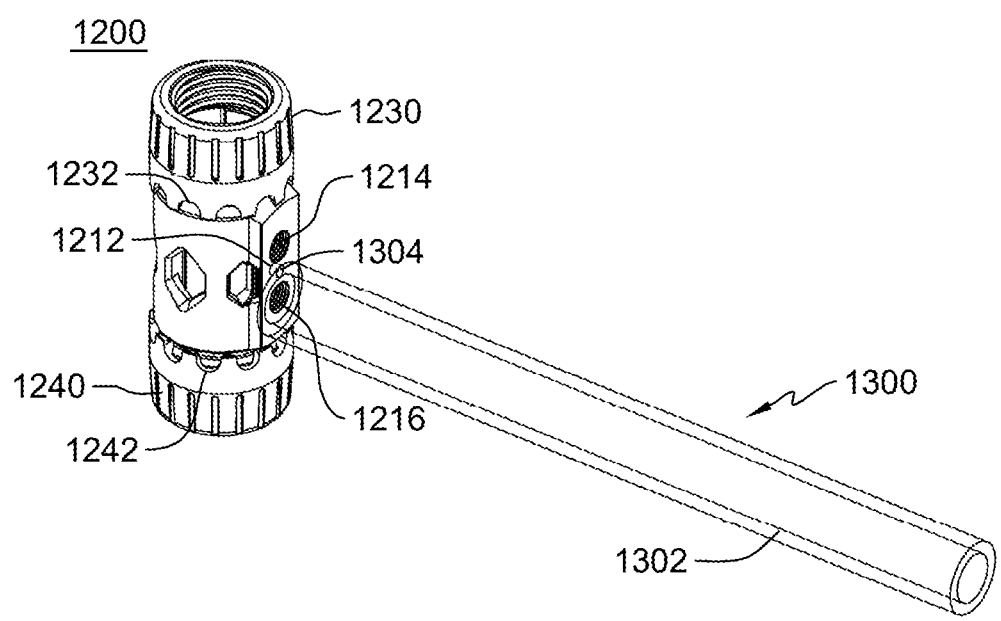
FIG. 41 is a perspective view of the system of FIG. 39 with a transparent insertion instrument, in accordance with an aspect of the present invention.

FIGS. 39-41 illustrate another embodiment of a vertebral body replacement system 1200. The system 1200 includes an implant 1202 and a drive mechanism 1300. The implant 1202 may include a body 1210, a first rotating member 1230 rotatably coupled to the first end of the body 1210, a second rotating member 1240 rotatably coupled to the second end of the body 1210, a first extension member (not shown) moveably coupled to the first end of the body 1210, and a second extension member (not shown) moveably coupled to a second end of the body 1210. The body 1210 include at least one opening 1212. The opening 1212 may be sized to engage the drive sleeve 1300. The first rotating member 1230 and the second rotating member 1240 may be of the type described above with reference to rotating members 730, 740, 930, 940 and which will not be described again here for brevity's sake. The first extension member (not shown) and second extension member (not shown) may be of the type described above with reference to extension members 750, 770, 950, 970 and which will not be described again here for brevity's sake.

The drive sleeve 1300 may include a body 1302 and a coupling protrusion 1304. The coupling protrusion engages the opening 1212 in the body 1210. The drive sleeve 1300 is then positioned for engagement with one of the rotating members 1230, 1240 to expand the implant 1202. Although not shown, a deployment handle, such as deployment handles 640, 650 as described in greater detail above, may be slid over the body 1302 to engage one of the rotating members 1230, 1240 to expand the implant 1202. Once a first rotating member 1230, 1240 is expanded, then the deployment handle (not shown) may be disengaged from the teeth 1232, 1242. Next, the drive sleeve 1300 may be rotated to a second position and the deployment handle (not shown) positioned to engage the second rotating member 1230, 1240 to expand the implant 1200. The implant 1200 may be secured in the expanded position by inserting locking mechanisms (not shown) into the openings 1214, 1216. One locking mechanism (not shown) may extend through the opening 1214 and engage at least a portion of the first extension member (not shown) to secure the first extension member in the desired expanded position. A second locking mechanism (not shown) may extend through the opening 1216 and engage at least a portion of the second extension member (not shown) to secure the second extension member in the desired expanded position.

Referring now to FIGS. 42-52, another vertebral body replacement implant 1500 is shown. The vertebral body implant 1500 may include a body 1510, a first rotating member 530 rotatably coupled to the first end 1512 of the body 1510, a second rotating member 540 rotatably coupled to the second end 1514 of the body 1510, a first extension member 1550 coupled to a first end 1512 of the body 1510, and the second extension member 1570 coupled to a second end 1514 of the body 1510. The first rotating member 530 and the second rotating member 540 are as described in greater detail above with reference to FIGS. 1-30 and will not be described again here for brevity's sake.

As shown in FIGS. 43, 44, 49 and 50, the body 1510 may include an opening 1516 extending from the first end 1512 to the second end 1514, for example, along the longitudinal axis of the body 1510. The opening 1516 may include at least two channels 1517, 1518, 1519, extending into the body 1510 from the opening 1516. At least one first channel 1517 may extend from the first end 1512 towards the second end 1514. At least one second channel 1518 may extend from the second end 1514 toward the first end 1512. At least one third channel 1519 may extend from the first end 1512 to the second end 1514. In the depicted embodiment, the at least one first channel 1517 may be one first channel 1517, that at least one second channel 1518 may be one second channel 1518, and the at least one third channel 1519 may be, for example, for channels 1519. The channels 1517, 1518, 1519 may be, for example, evenly spaced around the opening 1516. As shown, the body 1510 may include, for example, one first channel 1517 open on the first end 1512, one second channel 1518 open on the second end 1514, and four third channels 1519 open on both the first and second ends 1512, 1514. Alternative numbers of channels 1517, 1518, 1519 are also contemplated, for example, the body 1510 may include more or less channels 1517, 1518, 1519.

Figure 42:
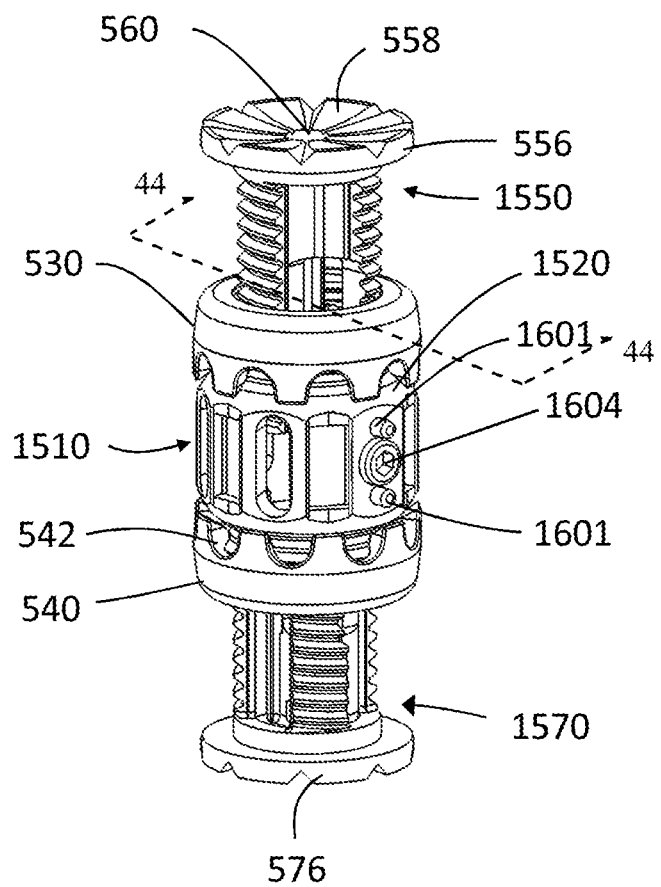
FIG. 42 is a perspective view of another vertebral body implant in an expanded position, in accordance with an aspect of the present invention.
Figure 43:
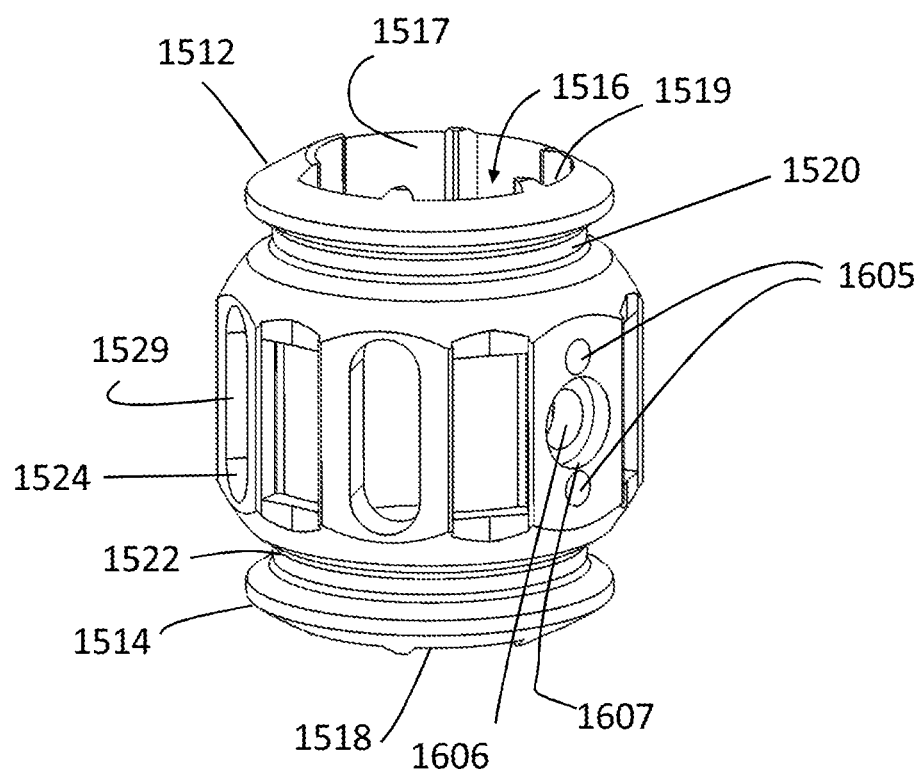
FIG. 43 is a perspective view of a body of the vertebral body implant of FIG. 42, in accordance with an aspect of the present invention.
Figure 49:
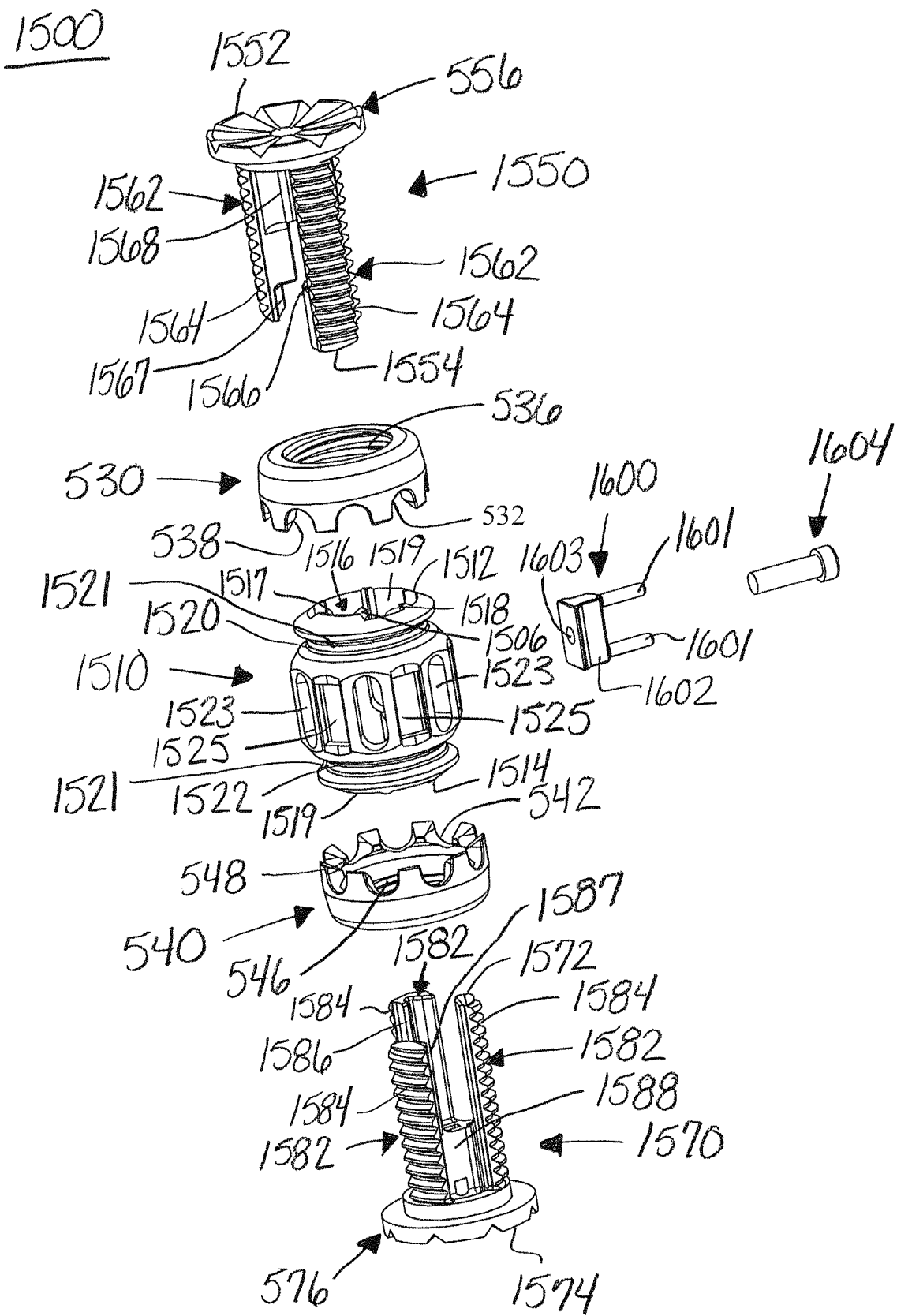
FIG. 49 is an exploded, perspective view of the vertebral body implant of FIG. 42, in accordance with an aspect of the present invention.
Figure 50:
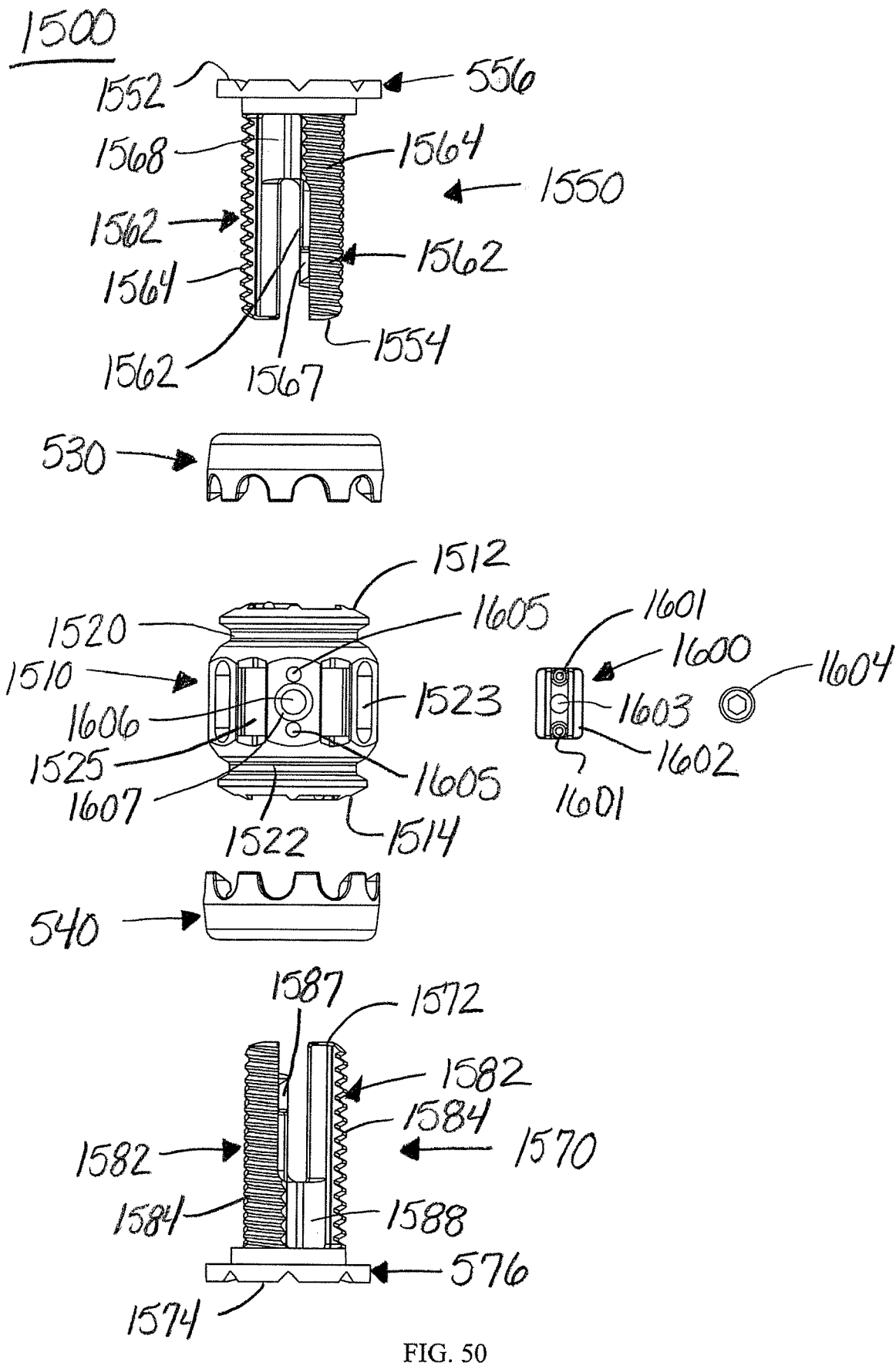
FIG. 50 is an exploded, side view of the vertebral body implant of FIG. 42, in accordance with an aspect of the present invention.

The exterior surface of the body 1510 may further include a first groove 1520 near the first end 1512 at a second groove 1522 near the second end 1514, as shown in FIGS. 43, 44, 49 and 50. The first and second grooves 1520, 1522 may extend around the circumference of the body 1510 and be sized to receive the first and second rotating members 530, 540, respectively. Each groove 1520, 1522 may include an opening 1521 for receiving a pin 1506. As shown in FIGS. 42-44, 49 and 50, the body 1510 may also include at least one aperture 1606 positioned around the circumference of the exterior surface. The at least one aperture 1606 may be positioned, for example, at a midpoint between the first end 1512 and the second end 1514 of the body 1510. The at least one aperture 1606 may be, for example, a threaded opening. The at least one aperture 1606 may also be surrounded by a recessed region or countersunk shelf 1607, as shown in FIGS. 43 and 50. The countersunk shelf 1607 allows a screw 1604 to be inserted into the body 1510 flush with the exterior surface of the body 1510. The body 1510 may also include at least one first guide pin hole 1605 superior to the aperture 1606 and at least one second guide pin hole 1605 inferior to the aperture 1606. The aperture 1606 may be sized and shaped to receive a fastener or screw 1604, as shown in FIGS. 42, 44, 49 and 50. The first guide pin hole 1605 and second guide pin hole 1605 may be sized and shaped to receive a locking insert 1600, as shown in FIGS. 42, 44, 49 and 50. In the depicted embodiment, one aperture 1606 surrounded by the first and second guide pin holes 1605 is shown, however, additional apertures 1606 and guide pin holes 1605 positioned around the circumference of the body 1510 are also contemplated. The body 1510 may further include openings 1523 positioned around the circumference of the body 1510. The openings 1523 may, for example, be separated by a gripping surface or recessed region 1525. The recessed regions 1525 may be used, for example, to couple to an insertion tool (not shown). As depicted, the three sets of openings 1605, 1606 may be positioned between recessed regions 1525.

Figure 45:
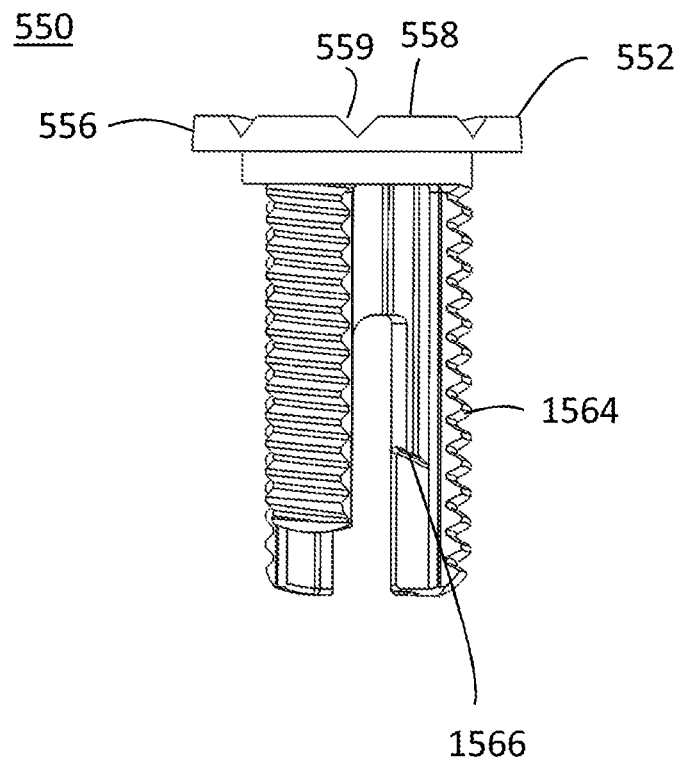
FIG. 45 is a side view of an extension member of the vertebral body implant of FIG. 42, in accordance with an aspect of the present invention.
Figure 46:
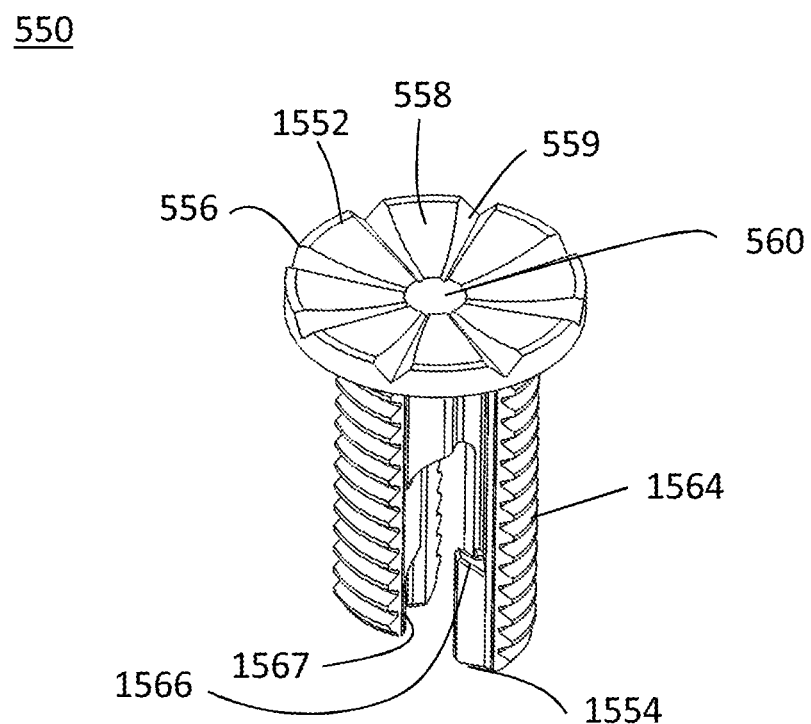
FIG. 46 is a top perspective view of the extension member of FIG. 45, in accordance with an aspect of the present invention.
Figure 47:
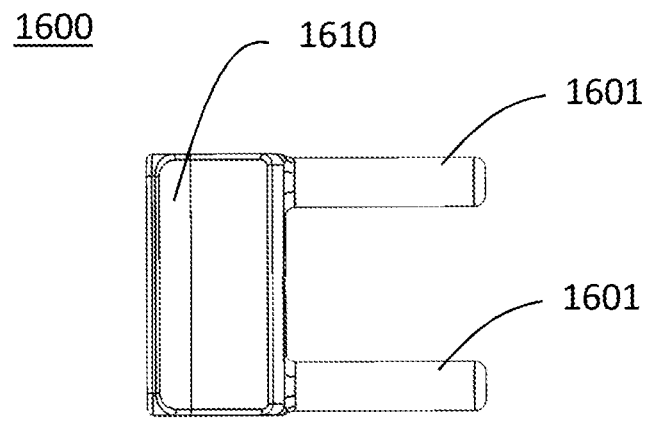
FIG. 47 is a side view of an internal locking member of the vertebral body implant of FIG. 42, in accordance with an aspect of the present invention.
Figure 48:
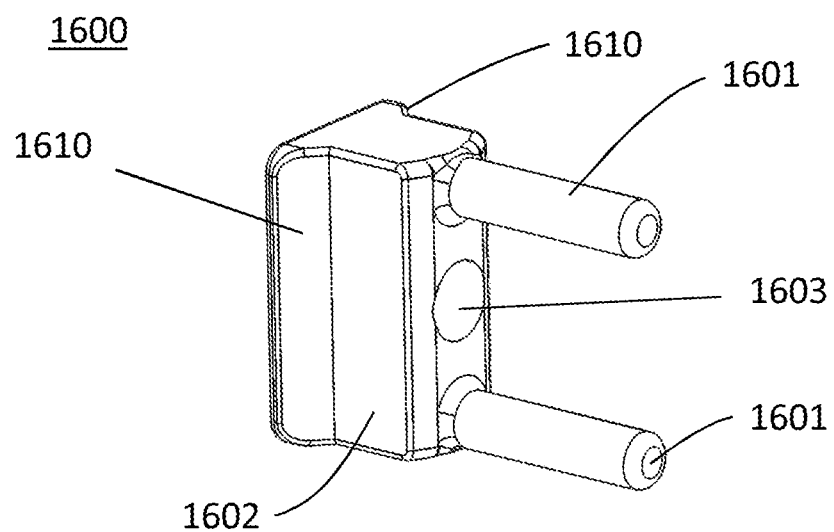
FIG. 48 is an end perspective view of the internal locking member of FIG. 47, in accordance with an aspect of the present invention.

Referring now to FIGS. 42, 45, 46, 49 and 50, the extension members 1550, 1570 are shown. FIGS. 45 and 46 show the first extension member 1550. The first extension member 1550 may include a first end 1552 and a second end 1554. The first extension member 1550 may also include a top portion or first end cap 556 at the first end 1552 and at least one leg member 1562 extending away from the top portion 556 and toward the second end 1554. The top portion 556 may include a curved top surface 558, grooves 559, and a center opening 560, as described in greater detail above with reference to implant 500 and which will not be described again here for brevity sake.

Figure 51:
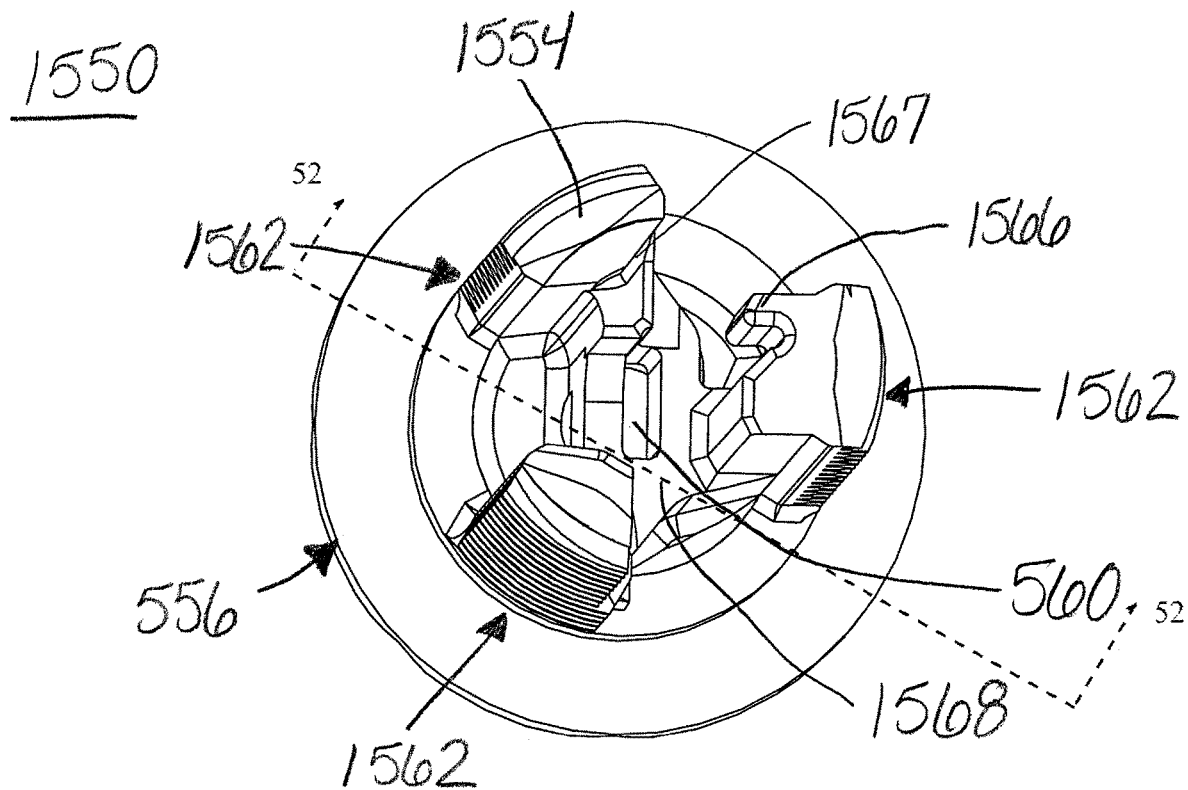
FIG. 51 is a perspective end view of the extension member of the vertebral body implant FIG. 42, in accordance with an aspect of the present invention.
Figure 52:
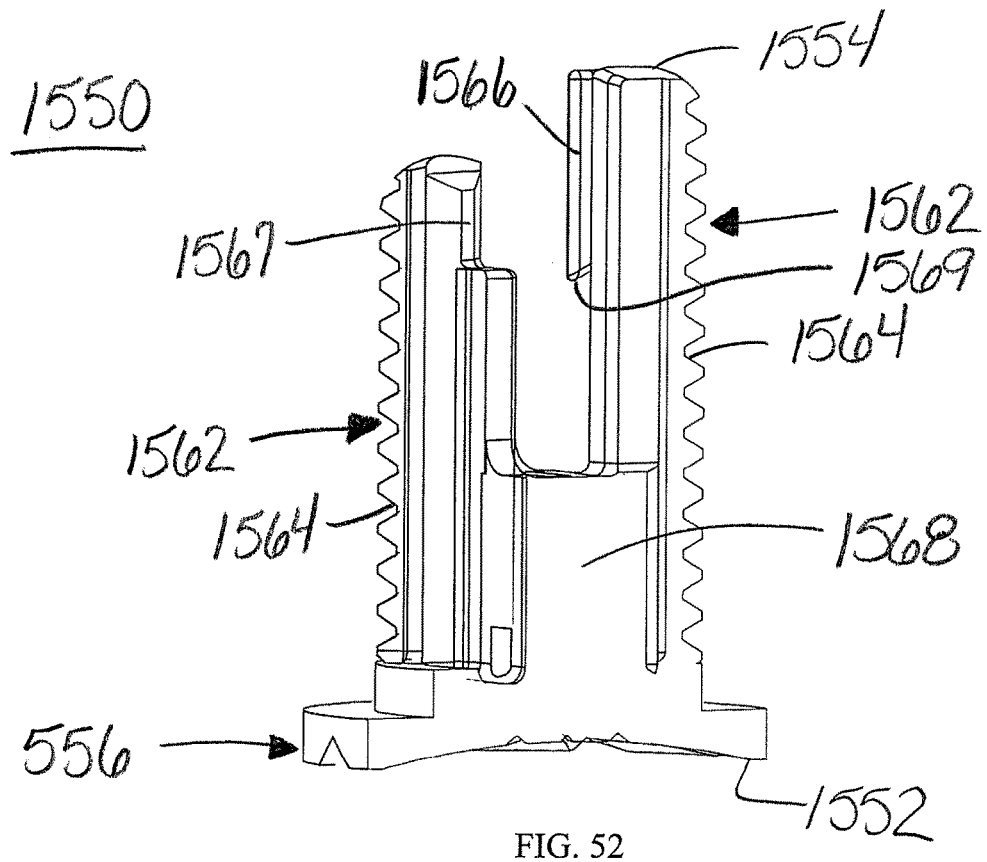
FIG. 52 is a side, cross-sectional view of the extension member taken along line 52-52 in FIG. 51, in accordance with an aspect of the present invention.

The at least one leg member 1562 may be, for example, three leg members 1562, as shown in FIGS. 49-51. The leg members 1562 may include threads 1564 on an exterior surface. The second end 1554 of the leg members 1562 may be, for example, tapered or angled. The leg members 1562 may include a short leg member 1562 and two longer leg members 1562. The short leg member 1562 may be received within the channel 1517 and include, for example, a recessed region 1567, as shown in FIGS. 46, 49, 51 and 52. A first longer leg member 1562 may include a protrusion or hook 1566 for engaging a channel 1519 in the body 1510. The protrusion 1566 may include an angled end 1569, as shown in FIG. 52, to engage at least one retention pin 1506 during use. The protrusion 1566 may have a recess positioned adjacent to the protrusion 1566 and the remaining interior surface of the leg member 1562 may extend into the center of the extension member 1550, for example, approximately the same distance as the protrusion 1566.

The threads 1564 on the legs 1562 engage the threads 536 on an interior surface of the first rotating member 530 to translate the leg member 1562 with respect to the body 1510. The threads 564 may extend from the second end 1554 to a bottom surface of the first end cap 556. The leg members 1562 may be curved to enable the leg members 1562 to rotate with respect to the first rotating member 530. The first extension member 1550 may also include at least one support member 1568 positioned between and connected to the leg members 1562. The at least one support member 1568 may be, for example, inset into the extension member 1550 with respect to the exterior surface of the leg members 1562. As depicted in FIGS. 51-52, the support members 1568 may, for example, form an inner structure surrounding the opening 560 to form an inner channel through the implant 1500. The arrangement of the leg members 1562 may be, for example, straight or curved between the leg members 1562.

The second extension member 1570, as shown in FIGS. 42, 49 and 50, may include a first end 1572 and a second end 1574. The second extension member 1570 may also include a bottom portion or second end cap 576 at the first end 1572 and at least one leg member 1582 extending away from the bottom portion 576 and to the first end 1572. The bottom portion 576 may include a curved bottom surface 578, grooves 579 and an opening 580, as described in greater detail above with reference to implant 500 and which will not be described again here for brevity's sake.

The at least one leg member 1582 may be, for example, three leg members 1582 and may include threads 1584, protrusion or hook 1586, and support members 1588. The threads 1584, protrusions 1586, and support members 1588 may be of the type described above with reference to threads 1564, protrusion or hook 1566, and support members 1568, which will not be described again here for brevity's sake. The first end 1572 of the leg members 1582 may be, for example, tapered or angled. The leg members 1582 may include a short leg member 1582 and two longer leg members 1582. The short leg member 1582 may be received within the channel 1518 and include, for example, a recessed region 1587, as shown in FIG. 49. A first longer leg member 1582 may include a protrusion or hook 1586 for engaging a channel 1519 in the body 1510. The protrusion 1586 may include an angled end to engage at least one retention pin 1506 during use. The protrusion 1586 may have a recess positioned adjacent to the protrusion 1586 and the remaining interior surface of the leg member 1582 may extend into the center of the extension member 1570, for example, approximately the same distance as the protrusion 1586.

The threads 1584 on the legs 1582 engage the threads 546 on an interior surface of the second rotating member 540 to translate the leg member 1582 with respect to the body 1510. The threads 1584 may extend from the first end 1572 to a bottom surface of the second end cap 576. The leg members 1582 may be curved to enable the leg members 1582 to rotate with respect to the second rotating member 540. The second extension member 1570 may also include at least one support member 1588 positioned between and connected to the leg members 1582. The at least one support member 1588 may be, for example, inset into the extension member 1570 with respect to the exterior surface of the leg members 1582. As shown with respect to extension member 1550 in FIGS. 51-52, the support members 1588 may, for example, form an inner structure surrounding the opening 580 to form an inner channel through the implant 1500. The arrangement of the leg members 1582 may be, for example, straight or curved between the leg members 1582.

Figure 44:
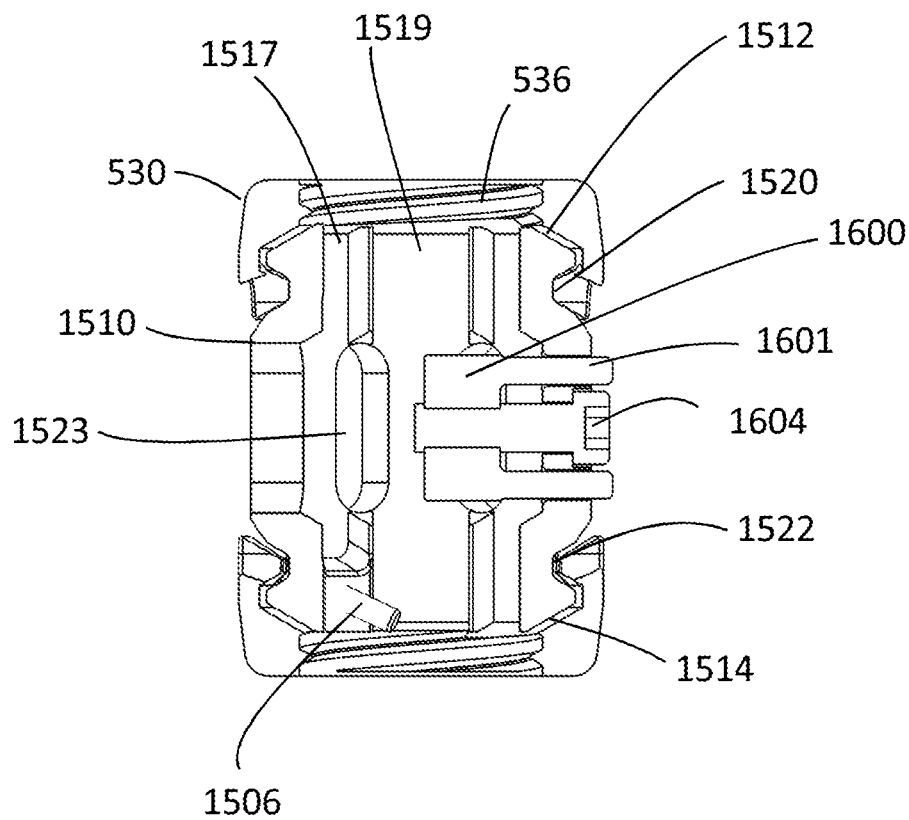
FIG. 44 is a cross-sectional view of the vertebral body implant of FIG. 42 taken along line 44-44 in FIG. 42 with the extension members removed, in accordance with an aspect of the present invention.

The implant 1500 may also include a locking mechanism, locking insert, or internal friction lock 1600, as shown in FIGS. 42, 44, and 47-50. The lock 1600 may include a body portion 1602 and guide pins 1601 coupled to the front side of the body portion 1602. As shown, the lock 1600 may include, for example, two guide pins 1601. The lock 1600 may also include a threaded opening 1603 for receiving a screw or fastener 1604, as shown in FIGS. 42 and 44. The threaded opening 1603 may extend through the body portion 1602 from a front side to a back side. The guide pins 1601 may extend away from the front side of the body portion 1602 above and below the threaded opening 1603. The body portion 1602 may also include two surfaces, friction surfaces, or press legs 1610 for engaging the interior wall of the body 1510. The back side of the body portion 1602 may be, for example, wider than the front side of the body portion 1602.

The vertebral body replacement device 1500 may be assembled by obtaining a body 1510 with a first rotating member 530 positioned in the first groove 1520 and a second rotating member 540 positioned in the second groove 1522. Next, the first and second extension members 1550, 1570 may be inserted into the channels 1517, 1518, 1519 in the opening 1516 of the body 1510. The first extension member 1550 may be inserted, for example, into the channels 1517, 1519 from the first end 1512. During insertion into the channels 1517, 1519, the protrusion 1566 of the first extension member 1550 may be aligned with at least one channel 1519 on the interior surface of the body 1510. The first extension member 1550 may be translated until the threads 1564 of the leg members 1562 engage the interior threads 1536 of the first rotating member 530. The first rotating member 530 may be rotated until the first extension member 1550 engages the first end 1512 of the body 1510. Once the first extension member 1550 is positioned in the body 1510, the second extension member 1570 may be inserted into the opening 1516, or vice versa. The second extension member 1570 may be inserted into the channels 1518, 1519 from the second end 1514. During insertion into the channels 1518, 1519, the protrusion 1586 of the second extension member 1570 may be aligned with at least one channel 1519 on the interior surface of the body 1510. The second rotating member 540 may be rotated until the second extension member 1570 engages the second end 1514 of the body 1510. The locking mechanism 1600 may be coupled to the implant 1500 using the locking holes 1605. The fastener 1604 may be coupled to the implant 1500 using the aperture

1524 and may be partially screwed into place, so that the locking mechanism 1600 is coupled to the implant 1500. Once a desired position has been achieved for the extension members 1550, 1570 of the implant 1500, the screw 1604 may be tightened to secure the locking mechanism 1600 to the body 1510 and fix the members of the implant 1500 from rotating.

As may be recognized by those of ordinary skill in the art based on the teachings herein, numerous changes and modifications may be made to the above-described and other embodiments of the present disclosure without departing from the scope of the disclosure. The implants, devices, systems, and their components as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices, implants and systems may include more or fewer components or features than the embodiments as described and illustrated herein. For example, the components and features of the vertebral body implants of FIGS. 1-30, FIGS. 31-34, FIGS. 35-36, FIGS. 37-38, FIGS. 39-41, and FIGS. 42-52 may all be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A vertebral body implant, comprising:
    a body with a first end and a second end, the body further comprising:
        at least one aperture positioned at a midpoint between the first end and the second end;
        at least one first locking hole positioned superior to the at least one aperture; and
        at least one second locking hole positioned inferior to the at least one aperture;
    at least one rotating member rotatably coupled to at least one of the first end and the second end, an end of the at least one rotating member comprises a plurality of notches inset into the at least one rotating member;
    at least one extension member moveably coupled to at least one of the first end and the second end; and
    a locking plate capable of being positioned against an interior wall of the body to engage the at least one extension member preventing further extension.

2. The vertebral body implant of claim 1, wherein the at least one rotating member comprises:
    a first rotating member rotatably coupled to the first end of the body, a second end of the first rotating member comprises a plurality of first notches inset into the first rotating member; and
    a second rotating member rotatably coupled to the second end of the body, a first end of the second rotating member comprises a plurality of second notches inset into the second rotating member; and
    wherein the at least one extension member comprises:
    a first extension member moveably coupled to the first end of the body; and
    a second extension member moveably coupled to the second end of the body.

3. The vertebral body implant of claim 1, the locking plate comprising:
    a first post positioned near a first end of the locking plate, wherein the first post is inserted into a locking hole of the at least one first locking hole,
    a second post positioned near a second end of the locking plate, wherein the second post is inserted into a locking hole of the at least one second locking hole, and
    a bore located between the first post and the second post, wherein the bore is concentric to the at least one aperture.

4. The vertebral body implant of claim 3, further comprising:
    a threaded fastener;
        the threaded fastener extending through the bore of the locking plate and the at least one aperture of the body; and
        the threaded fastener is capable of securing the locking plate against the interior wall of the body to engage the at least one extension member to prevent further extension.

5. The vertebral body implant of claim 2, the body further comprising:
    at least two solid faces and at least two bone grafting windows;
    the solid faces and bone grafting windows alternating around the body; and
    at least one solid face further comprises:
        an aperture of the at least one aperture, a locking hole of the at least one first locking hole, and a locking hole of the at least one second locking hole.

6. The vertebral body implant of claim 2, the first rotating member further comprising:
    a center opening forming an interior surface, the interior surface comprising:
        threads positioned on the interior surface; and the plurality of first notches opening toward an inferior end; and the second rotating member further comprising:
a center opening forming an interior surface, the interior surface comprising:
threads positioned on the interior surface; and
the plurality of second notches opening toward a superior end.

7. The vertebral body implant of claim 6, the first extension member further comprising:
a top portion;
at least one first leg member extending away from the top portion, the at least one first leg member further comprising:
threads positioned on an exterior surface of the at least one first leg member and configured to engage the threads on the interior surface of the first rotating member; and
a protrusion positioned on a second end of the at least one first leg member and configured to engage a stop member coupled to the body; and
at least one first support member positioned between and coupled to the at least one first leg member;
the second extension member further comprising:
a bottom portion;
at least one second leg member extending away from the bottom portion, the at least one second leg member further comprising:
threads positioned on an exterior surface of the at least one second leg member and configured to engage the threads on the interior surface of the second rotating member; and
a protrusion positioned on a first end of the at least one second leg member and configured to engage a pin coupled to the body; and
at least one second support member positioned between and coupled to the at least one second leg member.

8. An expandable cage system, comprising:
a vertebral body device, comprising:
a body with a first end and a second end, the body comprising:
at least one aperture positioned on the body along a midpoint between the first end and the second end;
at least one first locking hole positioned superior to the at least one aperture between the at least one aperture and the first end; and
at least one second locking hole positioned inferior to the at least one aperture between the at least one aperture and the second end;
at least one rotating member rotatably coupled to at least one of the first end and the second end of the body;
at least one extension member moveably coupled to an end of the body; and
a locking plate capable of being positioned against an interior wall of the body to engage the at least one extension member preventing further extension; and
an insertion instrument, the insertion instrument being sized to surround the at least one aperture, the at least one first locking hole, and the at least one second locking hole.

9. The expandable cage system of claim 8, wherein the insertion instrument comprises:
a gripping member;
a compression sleeve sized to engage the gripping member; and
at least one rotating member sized to receive the compression sleeve and gripping member.

10. The expandable cage system of claim 9, the body further comprising:
at least one opening positioned on each side of the at least one aperture, the at least one opening being adapted for insertion and engaging of the gripping member.

11. The expandable cage system of claim 9, the at least one rotating member of the insertion instrument further comprising:
a first end having a plurality of projections positioned around a circumference of the first end.

12. The expandable cage system of claim 9, the at least one rotating member of the insertion instrument further comprising:
a first end having a first semi-circular protrusion and a plurality of projections positioned around the first protrusion on the first end.

13. The expandable cage system of claim 12, where the at least one rotating member of the insertion instrument further comprises:
a second end having a second semi-circular protrusion extending away from the second end and aligned with the first semi-circular protrusion around a circumference of the rotating member of the insertion instrument.

14. A method of using an expandable cage system, comprising:
obtaining a vertebral body implant, the vertebral body implant comprising:
a body with a first end and a second end, the body further comprising:
at least one aperture positioned at a midpoint between the first end and the second end;
at least one first locking hole positioned superior to the at least one aperture; and
at least one second locking hole positioned inferior to the at least one aperture;
at least one rotating member rotatably coupled to an end of the body;
at least one extension member moveably coupled to an end of the body;
obtaining an insertion instrument; and
a locking plate capable of being positioned against an interior wall of the body to engage the at least one extension member preventing further extension;
coupling the vertebral body implant to the insertion instrument;
inserting the vertebral body implant into a patient between two vertebral bodies;
expanding the vertebral body implant; and
removing the insertion instrument.

15. The method of claim 14, the insertion instrument comprising:
a gripping member;
a compression sleeve sized to engage the gripping member; and
at least one rotating member sized to receive the compression sleeve and gripping member.

16. The method of claim 15, the method further comprising:
inserting a locking member into the body of the vertebral body implant.

17. The method of claim 15, expanding the vertebral body implant further comprising:
rotating the at least one rotating member of the insertion instrument in a first direction to engage and rotate the at least one rotating member of the vertebral body implant, rotating the at least one rotating member of the vertebral body implant translates the coupled at least one extension member to increase a height of the vertebral body implant.

18. The method of claim 14, the at least one extension member comprising a first extension member and a second extension member; and
expanding the vertebral body implant further comprising:
expanding only one of the first extension member and the second extension member.

19. The method of claim 15, the at least one rotating member of the insertion instrument further comprising:
a first end having a semi-circular protrusion and a plurality of projections positioned around the semi-circular protrusion on the first end, where the semi-circular protrusion engages one of a first rotating member of the at least one rotating member and a second rotating member of the at least one rotating member to expand one of a first extension member of the at least one extension member and a second extension member of the at least one extension member.

20. The method of claim 14, further comprising:
securing a locking member of the vertebral body implant comprising:
inserting a threaded fastener through a bore in the locking member and an aperture of the at least one aperture in the body of the vertebral body implant; and
tightening the threaded fastener to insert a first post of the locking member into the at least one first locking hole superior to the at least one aperture and to insert a second post of the locking member into the at least one second locking hole inferior to the at least one aperture, the locking member engaging the at least one extension member to secure the vertebral body implant in an expanded position.

* * * * *